US008741286B2

(12) United States Patent
Christophe et al.

(10) Patent No.: US 8,741,286 B2
(45) **Date of Patent: *Jun. 3, 2014**

(54) SERENE PROTEASE DERIVATIVES AND USES IN THE PREVENTION OR THE TREATMENT OF BLOOD COAGULATION DISORDERS

(71) Applicant: Institut National de la Sante et de la Recherche Medicale (INSERM), Paris Cedex (FR)

(72) Inventors: Olivier Christophe, Le Kremlin Bicetre Cedex (FR); Cecile Denis, Le Kremlin Bicetre Cedex (FR); Ghislaine Cherel, Le Kremlin Bicetre Cedex (FR); Paul Gueguen, Brest Cedex (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/909,323

(22) Filed: Jun. 4, 2013

(65) Prior Publication Data

US 2013/0261060 A1 Oct. 3, 2013

Related U.S. Application Data

(63) Continuation of application No. 13/732,465, filed on Jan. 2, 2013, now Pat. No. 8,518,400, which is a continuation of application No. 13/139,367, filed as application No. PCT/EP2009/067632 on Dec. 21, 2009, now Pat. No. 8,436,144.

(60) Provisional application No. 61/222,960, filed on Jul. 3, 2009.

(30) Foreign Application Priority Data

Dec. 19, 2008 (EP) .................................... 08305990
Apr. 23, 2009 (EP) .................................... 09305349

(51) Int. Cl.
*A61K 35/14* (2006.01)
*A61K 38/48* (2006.01)
*C07H 21/04* (2006.01)

(52) U.S. Cl.
USPC ........ 424/94.64; 435/219; 530/381; 536/23.2

(58) Field of Classification Search
None
See application file for complete search history.

(56) References Cited

U.S. PATENT DOCUMENTS

| | | | | |
|---|---|---|---|---|
| 8,436,144 | B2 * | 5/2013 | Christophe et al. | 530/381 |
| 8,518,400 | B2 * | 8/2013 | Christophe et al. | 424/94.64 |
| 2006/0148038 | A1 | 7/2006 | Louvain | |

FOREIGN PATENT DOCUMENTS

| | | |
|---|---|---|
| EP | 1 820 508 | 8/2007 |
| WO | 03/035861 | 5/2003 |
| WO | 2006/018204 | 2/2006 |

OTHER PUBLICATIONS

Louvain-Quintard et al.; "Thrombin-Activable Factor X Re-establishes an Intrinsic Amplification in Tenase-Deficient Plasmas"; The Journal of Biological Chemistry, vol. 280, No. 50, pp. 41352-41359, Dec. 16, 2005.

Baugh et al.; "Role of the Activation Peptide Domain in Human Factor X Activation by the Extrinsic Xase Complex"; The Journal of Biological Chemistry, vol. 271, No. 27, pp. 16126-16134, Jul. 5, 2996.

Nakagawa et al.; "Identification of the Oligosaccharide Structures of Human Coagulation Factor X Activation Peptide at Each Glycosylation Site"; Glycoconjugate Journal, vol. 12, No. 2, pp. 173-181, Apr. 1995.

Rudolph et al.; "The Role of the Factor X Activation Peptide: A Deletion Mutagenesis Approach"; Thrombosis and Haemostasis; Stuttgart, DE, vol. 88, No. 5, pp. 756-762, Nov. 1, 2002.

* cited by examiner

*Primary Examiner* — Nashaat Nashed
(74) *Attorney, Agent, or Firm* — Whitham Curtis Christofferson & Cook, PC

(57) ABSTRACT

The present invention relates to chimeric derivatives of serine protease zymogen containing the activation peptide of factor X or a fragment thereof for improving the half-life of said derivatives. Preferably, said chimeric derivatives are protein C and factor X derivatives. The invention also relates to said derivatives for the prevention or treatment of blood coagulation disorders.

11 Claims, 12 Drawing Sheets

Figure 4:
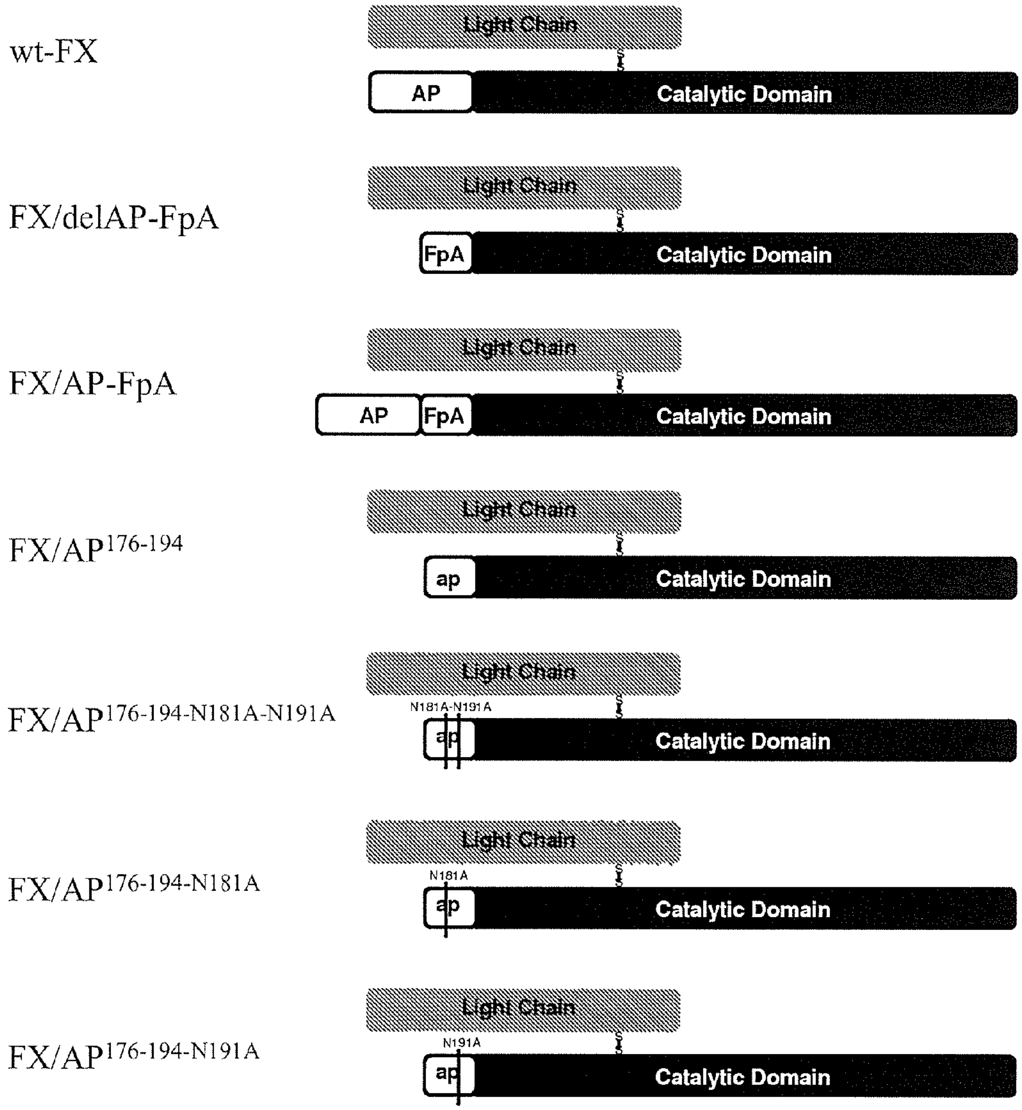

-40 Met-Gly-Arg-Pro-Leu-His-Leu-Val-Leu-Leu-Ser-Ala-Ser-Leu-Ala-Gly-Leu-Leu-Leu-Leu -21
1 20
-20 Gly-Glu-Ser-Leu-Phe-Ile-Arg-Arg-Glu-Gln-Ala-Asn-Asn-Ile-Leu-Ala-Arg-Val-Thr-Arg -1
21 40
1 Ala-Asn-Ser-Phe-Leu-Glu-Glu-Met-Lys-Lys-Gly-His-Leu-Glu-Arg-Glu-Cys-Met-Glu-Glu 20
41 60
21 Thr-Cys-Ser-Tyr- Glu-Glu-Ala-Arg-Glu-Val-Phe-Glu Asp-Ser-Asp-Lys-Thr-Asn-Glu-Phe 40
61 80
41 Trp-Asn-Lys-Tyr-Lys-Asp-Gly-Asp-Gln-Cys-Glu-Thr-Ser-Pro-Cys-Gln-Asn-Gln-Gly-Lys 60
81 100
61 Cys-Lys-Asp-Gly-Leu-Gly-Glu-Tyr-Thr-Cys-Thr-Cys-Leu-Glu-Gly-Phe-Glu-Gly-Lys-Asn 80
101 120
81 Cys-Glu-Leu-Phe-Thr-Arg-Lys-Leu-Cys-Ser-Leu-Asp-Asn-Gly-Asp-Cys-Asp-Gln-Phe-Cys 100
121 140
101 His-Glu-Glu-Gln-Asn-Ser-Val-Val-Cys-Ser-Cys-Ala-Arg-Gly-Tyr-Thr-Leu-Ala-Asp-Asn 120
141 160
121 Gly-Lys-Ala-Cys-Ile-Pro-Thr-Gly-Pro-Tyr-Pro-Cys-Gly-Lys-Gln-ThrLeu-Glu-Arg-Arg 140
161 180
141 Lys-Arg-Ser-Val-Ala-Gln-Ala-Thr-Ser-Ser-Ser-Gly-Glu-Ala-Pro-Asp-Ser-Ile-Thr-Trp 160
181 200
161 Lys-Pro-Tyr-Asp-Ala-Ala-Asp-Leu-Asp-Pro-Thr-Glu-Asn-Pro-Phe-Asp-Leu-Leu-Asp-Phe 180
201 220
181 Asn*-Gln-Thr-Gln-Pro-Glu-Arg-Gly-Asp-Asn-Asn*-Leu-Thr-Arg-Ile-Val-Gly-Gly-Gln-Glu 200
221 240
201 Cys-Lys-Asp-Gly-Glu-Cys-Pro-Trp-Gln-Ala-Leu-Leu-Ile-Asn-Glu-Glu-Asn-Glu-Gly-Phe 220
241 260
221 Cys-Gly-Gly-Thr-Ile-Leu-Ser-Glu-Phe-Tyr-Ile-Leu-Thr-Ala-Ala-His-Cys-Leu-Tyr-Gln 240
261 280
241 Ala-Lys-Arg-Phe-Lys-Val-Arg-Val-Gly-Asp-Arg-Asn-Thr-Glu-Gln-Glu-Glu-Gly-Gly-Glu 260
281 300
261 Ala-Val-His-Glu-Val-Glu-Val-Val-Ile-Lys-His-Asn-Arg-Phe-Thr-Lys-Glu-Thr-Tyr-Asp 280
301 320
281 Phe-Asp-Ile-Ala-Val-Leu-Arg-Leu-Lys-Thr-Pro-Ile-Thr-Phe-Arg-Met-Asn-Val-Ala-Pro 300
321 340
301 Ala-Cys-Leu-Pro-Glu-Arg-Asp-Trp-Ala-Glu-Ser-Thr-Leu-Met-Thr-Gln-Lys-Thr-Gly-Ile 320
341 360
321 Val-Ser-Gly-Phe-Gly-Arg-Thr-His-Glu-Lys-Gly-Arg-Gln-Ser-Thr-Arg-Leu-Lys-Met-Leu 340
361 380
341 Glu-Val-Pro-Tyr-Val-Asp-Arg-Asn-Ser-Cys-Lys-Leu-Ser-Ser-Ser-Phe-Ile-Ile-Thr-Gln 360
381 400
361 Asn-Met-Phe-Cys-Ala-Gly-Tyr-Asp-Thr-Lys-Gln-Glu-Asp-Ala-Cys-Gln-Gly-Asp-Ser-Gly 380
401 420
381 Gly-Pro-His-Val-Thr-Arg-Phe-Lys-Asp-Thr-Tyr-Phe-Val-Thr-Gly-Ile-Val-Ser-Trp-Gly 400
421 440
401 Glu-Gly-Cys-Ala-Arg-Lys-Gly-Lys-Tyr-Gly-Ile-Tyr-Thr-Lys-Val-Thr-Ala-Phe-Leu-Lys 420
441 460
421 Trp-Ile-Asp-Arg-Ser-Met-Lys-Thr-Arg-Gly-Leu-Pro-Lys-Ala-Lys-Ser-His-Ala-Pro-Glu 440
461 480
461 Val-Ile-Thr-Ser-Ser-Pro-Leu-Lys
481

Figure 1

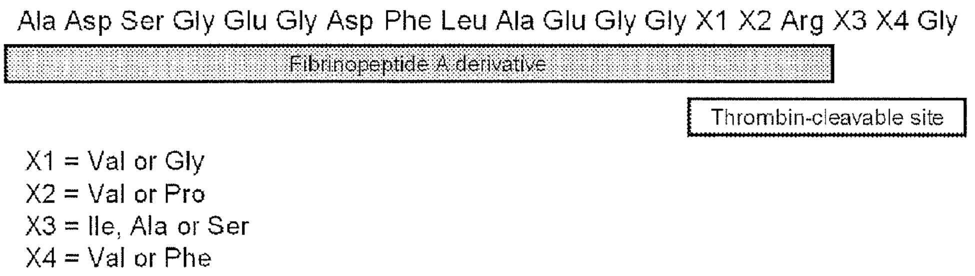
Figure 2A
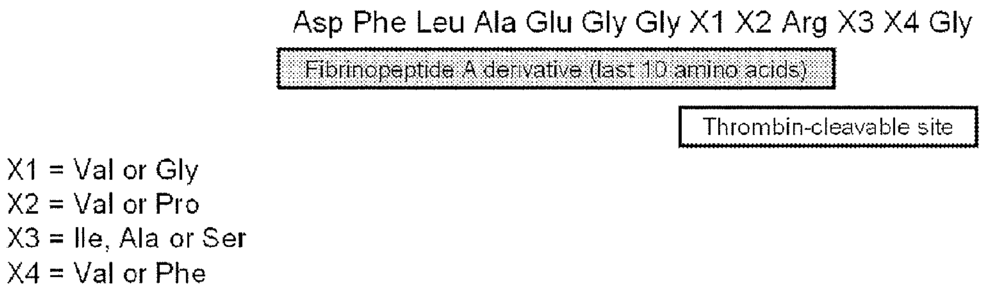
Figure 2B
Figure 2
Ala Asp Ser Gly Glu Gly Asp Phe Leu Ala Glu Gly Gly X1 X2 Arg X3 X4 Gly
Fibrinopeptide A derivative
Thrombin-cleavable site
X1 = Val or Gly
X2 = Val or Pro
X3 = Ile, Ala or Ser
X4 = Val or Phe
Asp Phe Leu Ala Glu Gly Gly X1 X2 Arg X3 X4 Gly
Fibrinopeptide A derivative (last 10 amino acids)
Thrombin-cleavable site
X1 = Val or Gly
X2 = Val or Pro
X3 = Ile, Ala or Ser
X4 = Val or Phe

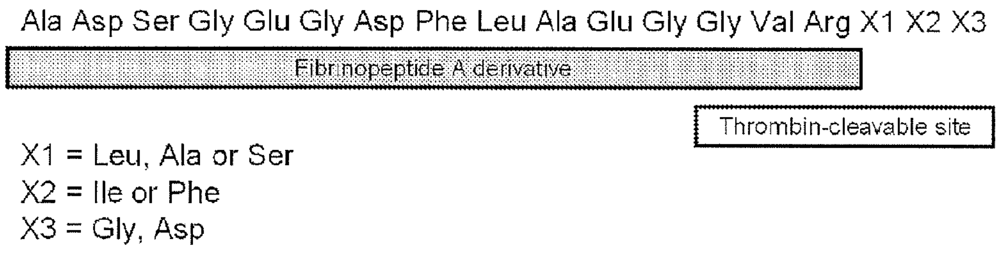
Figure 3A
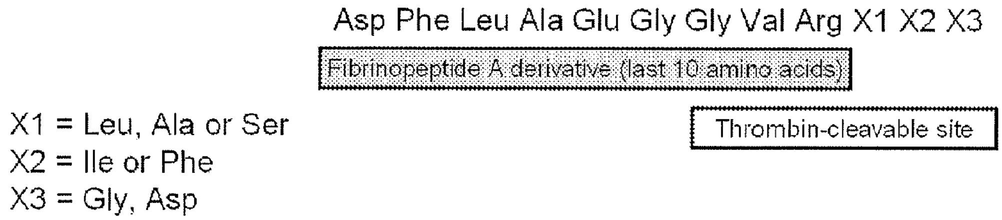
Figure 3B
Figure 3
Ala Asp Ser Gly Glu Gly Asp Phe Leu Ala Glu Gly Gly Val Arg X1 X2 X3
Fibrinopeptide A derivative
Thrombin-cleavable site
X1 = Leu, Ala or Ser
X2 = Ile or Phe
X3 = Gly, Asp
Asp Phe Leu Ala Glu Gly Gly Val Arg X1 X2 X3
Fibrinopeptide A derivative (last 10 amino acids)
Thrombin-cleavable site
X1 = Leu, Ala or Ser
X2 = Ile or Phe
X3 = Gly, Asp

SEQUENCE LISTING

```
<160> NUMBER OF SEQ ID NOS: 36

<210> SEQ ID NO 1
<211> LENGTH: 488
<212> TYPE: PRT
<213> ORGANISM: Homo sapiens

<400> SEQUENCE: 1

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45
```

-continued

```
Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
```

```
465                 470                 475                 480

Val Ile Thr Ser Ser Pro Leu Lys
                485


<210> SEQ ID NO 2
<211> LENGTH: 52
<212> TYPE: PRT
<213> ORGANISM: Homo sapiens

<400> SEQUENCE: 2

Ser Val Ala Gln Ala Thr Ser Ser Ser Gly Glu Ala Pro Asp Ser Ile
1               5                   10                  15

Thr Trp Lys Pro Tyr Asp Ala Ala Asp Leu Asp Pro Thr Glu Asn Pro
            20                  25                  30

Phe Asp Leu Leu Asp Phe Asn Gln Thr Gln Pro Glu Arg Gly Asp Asn
        35                  40                  45

Asn Leu Thr Arg
    50


<210> SEQ ID NO 3
<211> LENGTH: 461
<212> TYPE: PRT
<213> ORGANISM: Homo sapiens

<400> SEQUENCE: 3

Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
    50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
    130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
    210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255
```

```
Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
    290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
        355                 360                 365

Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
    450                 455                 460


<210> SEQ ID NO 4
<211> LENGTH: 16
<212> TYPE: PRT
<213> ORGANISM: Homo sapiens

<400> SEQUENCE: 4

Ala Asp Ser Gly Glu Gly Asp Phe Leu Ala Glu Gly Gly Gly Val Arg
1               5                   10                  15


<210> SEQ ID NO 5
<211> LENGTH: 19
<212> TYPE: PRT
<213> ORGANISM: Artificial
<220> FEATURE:
<223> OTHER INFORMATION: Polypeptide
<220> FEATURE:
<221> NAME/KEY: MISC_FEATURE
<222> LOCATION: (14)..(14)
<223> OTHER INFORMATION: X is G or V
<220> FEATURE:
<221> NAME/KEY: MISC_FEATURE
<222> LOCATION: (15)..(15)
<223> OTHER INFORMATION: X is V or P
<220> FEATURE:
<221> NAME/KEY: MISC_FEATURE
<222> LOCATION: (17)..(17)
<223> OTHER INFORMATION: X is I, A or S
<220> FEATURE:
<221> NAME/KEY: MISC_FEATURE
<222> LOCATION: (18)..(18)
<223> OTHER INFORMATION: X is V or F

<400> SEQUENCE: 5

Ala Asp Ser Gly Glu Gly Asp Phe Leu Ala Glu Gly Gly Xaa Xaa Arg
1               5                   10                  15
```

-continued

Xaa Xaa Gly

<210> SEQ ID NO 6
<211> LENGTH: 13
<212> TYPE: PRT
<213> ORGANISM: Artificial
<220> FEATURE:
<223> OTHER INFORMATION: Polypeptide
<220> FEATURE:
<221> NAME/KEY: MISC_FEATURE
<222> LOCATION: (8)..(8)
<223> OTHER INFORMATION: X is V or G
<220> FEATURE:
<221> NAME/KEY: MISC_FEATURE
<222> LOCATION: (9)..(9)
<223> OTHER INFORMATION: X is V or P
<220> FEATURE:
<221> NAME/KEY: MISC_FEATURE
<222> LOCATION: (11)..(11)
<223> OTHER INFORMATION: X is I, A or S
<220> FEATURE:
<221> NAME/KEY: MISC_FEATURE
<222> LOCATION: (12)..(12)
<223> OTHER INFORMATION: X is V or F

<400> SEQUENCE: 6

Asp Phe Leu Ala Glu Gly Gly Xaa Xaa Arg Xaa Xaa Gly
1               5                   10

<210> SEQ ID NO 7
<211> LENGTH: 13
<212> TYPE: PRT
<213> ORGANISM: Artificial
<220> FEATURE:
<223> OTHER INFORMATION: Polypeptide

<400> SEQUENCE: 7

Asp Phe Leu Ala Glu Gly Gly Gly Val Arg Ile Val Gly
1               5                   10

<210> SEQ ID NO 8
<211> LENGTH: 13
<212> TYPE: PRT
<213> ORGANISM: Artificial
<220> FEATURE:
<223> OTHER INFORMATION: Polypeptide

<400> SEQUENCE: 8

Asp Phe Leu Ala Glu Gly Gly Gly Val Arg Ala Val Gly
1               5                   10

<210> SEQ ID NO 9
<211> LENGTH: 13
<212> TYPE: PRT
<213> ORGANISM: Artificial
<220> FEATURE:
<223> OTHER INFORMATION: Polypeptide

<400> SEQUENCE: 9

Asp Phe Leu Ala Glu Gly Gly Gly Val Arg Ser Val Gly
1               5                   10

<210> SEQ ID NO 10
<211> LENGTH: 13
<212> TYPE: PRT
<213> ORGANISM: Artificial
<220> FEATURE:
<223> OTHER INFORMATION: Polypeptide

<400> SEQUENCE: 10

-continued

```
Asp Phe Leu Ala Glu Gly Gly Gly Val Arg Ile Phe Gly
1               5                   10


<210> SEQ ID NO 11
<211> LENGTH: 13
<212> TYPE: PRT
<213> ORGANISM: Artificial
<220> FEATURE:
<223> OTHER INFORMATION: Polypeptide

<400> SEQUENCE: 11

Asp Phe Leu Ala Glu Gly Gly Gly Val Arg Ala Phe Gly
1               5                   10


<210> SEQ ID NO 12
<211> LENGTH: 13
<212> TYPE: PRT
<213> ORGANISM: Artificial
<220> FEATURE:
<223> OTHER INFORMATION: Polypeptide

<400> SEQUENCE: 12

Asp Phe Leu Ala Glu Gly Gly Gly Val Arg Ser Phe Gly
1               5                   10


<210> SEQ ID NO 13
<211> LENGTH: 19
<212> TYPE: PRT
<213> ORGANISM: Artificial
<220> FEATURE:
<223> OTHER INFORMATION: Polypeptide
<220> FEATURE:
<221> NAME/KEY: MISC_FEATURE
<222> LOCATION: (17)..(17)
<223> OTHER INFORMATION: X is L, A or S
<220> FEATURE:
<221> NAME/KEY: MISC_FEATURE
<222> LOCATION: (18)..(18)
<223> OTHER INFORMATION: X is I or F
<220> FEATURE:
<221> NAME/KEY: MISC_FEATURE
<222> LOCATION: (19)..(19)
<223> OTHER INFORMATION: X is G or D

<400> SEQUENCE: 13

Ala Asp Ser Gly Glu Gly Asp Phe Leu Ala Glu Gly Gly Gly Val Arg
1               5                   10                  15

Xaa Xaa Xaa


<210> SEQ ID NO 14
<211> LENGTH: 13
<212> TYPE: PRT
<213> ORGANISM: Artificial
<220> FEATURE:
<223> OTHER INFORMATION: Polypeptide
<220> FEATURE:
<221> NAME/KEY: MISC_FEATURES
<222> LOCATION: (11)..(11)
<223> OTHER INFORMATION: X is L, A or S
<220> FEATURE:
<221> NAME/KEY: MISC_FEATURES
<222> LOCATION: (12)..(12)
<223> OTHER INFORMATION: X is I or F
<220> FEATURE:
<221> NAME/KEY: MISC_FEATURES
<222> LOCATION: (13)..(13)
<223> OTHER INFORMATION: X is G or D

<400> SEQUENCE: 14

Asp Phe Leu Ala Glu Gly Gly Gly Val Arg Xaa Xaa Xaa
1               5                   10
```

<210> SEQ ID NO 15
<211> LENGTH: 13
<212> TYPE: PRT
<213> ORGANISM: Artificial
<220> FEATURE:
<223> OTHER INFORMATION: Polypeptide

<400> SEQUENCE: 15

```
Asp Phe Leu Ala Glu Gly Gly Gly Val Arg Leu Ile Asp
1               5                   10
```

<210> SEQ ID NO 16
<211> LENGTH: 13
<212> TYPE: PRT
<213> ORGANISM: Artificial
<220> FEATURE:
<223> OTHER INFORMATION: Polypeptide

<400> SEQUENCE: 16

```
Asp Phe Leu Ala Glu Gly Gly Gly Val Arg Leu Ile Gly
1               5                   10
```

<210> SEQ ID NO 17
<211> LENGTH: 13
<212> TYPE: PRT
<213> ORGANISM: Artificial
<220> FEATURE:
<223> OTHER INFORMATION: Polypeptide

<400> SEQUENCE: 17

```
Asp Phe Leu Ala Glu Gly Gly Gly Val Arg Ala Ile Asp
1               5                   10
```

<210> SEQ ID NO 18
<211> LENGTH: 13
<212> TYPE: PRT
<213> ORGANISM: Artificial
<220> FEATURE:
<223> OTHER INFORMATION: Polypeptide

<400> SEQUENCE: 18

```
Asp Phe Leu Ala Glu Gly Gly Gly Val Arg Ala Ile Gly
1               5                   10
```

<210> SEQ ID NO 19
<211> LENGTH: 13
<212> TYPE: PRT
<213> ORGANISM: Artificial
<220> FEATURE:
<223> OTHER INFORMATION: Polypeptide

<400> SEQUENCE: 19

```
Asp Phe Leu Ala Glu Gly Gly Gly Val Arg Ser Ile Asp
1               5                   10
```

<210> SEQ ID NO 20
<211> LENGTH: 13
<212> TYPE: PRT
<213> ORGANISM: Artificial
<220> FEATURE:
<223> OTHER INFORMATION: Polypeptide

<400> SEQUENCE: 20

```
Asp Phe Leu Ala Glu Gly Gly Gly Val Arg Ser Ile Gly
1               5                   10
```

```
<210> SEQ ID NO 21
<211> LENGTH: 13
<212> TYPE: PRT
<213> ORGANISM: Artificial
<220> FEATURE:
<223> OTHER INFORMATION: Polypeptide

<400> SEQUENCE: 21

Asp Phe Leu Ala Glu Gly Gly Gly Val Arg Ala Phe Asp
1               5                   10


<210> SEQ ID NO 22
<211> LENGTH: 13
<212> TYPE: PRT
<213> ORGANISM: Artificial
<220> FEATURE:
<223> OTHER INFORMATION: Polypeptide

<400> SEQUENCE: 22

Asp Phe Leu Ala Glu Gly Gly Gly Val Arg Ala Phe Gly
1               5                   10


<210> SEQ ID NO 23
<211> LENGTH: 13
<212> TYPE: PRT
<213> ORGANISM: Artificial
<220> FEATURE:
<223> OTHER INFORMATION: Polypeptide

<400> SEQUENCE: 23

Asp Phe Leu Ala Glu Gly Gly Gly Val Arg Ser Phe Asp
1               5                   10


<210> SEQ ID NO 24
<211> LENGTH: 13
<212> TYPE: PRT
<213> ORGANISM: Artificial
<220> FEATURE:
<223> OTHER INFORMATION: Polypeptide

<400> SEQUENCE: 24

Asp Phe Leu Ala Glu Gly Gly Gly Val Arg Ser Phe Gly
1               5                   10


<210> SEQ ID NO 25
<211> LENGTH: 13
<212> TYPE: PRT
<213> ORGANISM: Artificial
<220> FEATURE:
<223> OTHER INFORMATION: Polypeptide

<400> SEQUENCE: 25

Asp Phe Leu Ala Glu Gly Gly Gly Val Arg Leu Phe Asp
1               5                   10


<210> SEQ ID NO 26
<211> LENGTH: 13
<212> TYPE: PRT
<213> ORGANISM: Artificial
<220> FEATURE:
<223> OTHER INFORMATION: Polypeptide

<400> SEQUENCE: 26

Asp Phe Leu Ala Glu Gly Gly Gly Val Arg Leu Phe Gly
1               5                   10


<210> SEQ ID NO 27
<211> LENGTH: 12
```

<212> TYPE: PRT
<213> ORGANISM: Artificial
<220> FEATURE:
<223> OTHER INFORMATION: Polypeptide

<400> SEQUENCE: 27

Glu Asp Gln Val Asp Pro Arg Leu Ile Asp Gly Lys
1 5 10

<210> SEQ ID NO 28
<211> LENGTH: 45
<212> TYPE: DNA
<213> ORGANISM: Artificial
<220> FEATURE:
<223> OTHER INFORMATION: Primers

<400> SEQUENCE: 28
ctggaacgcc ggaagaggga cctgcttgac ttcaaccaga cgcag 45

<210> SEQ ID NO 29
<211> LENGTH: 45
<212> TYPE: DNA
<213> ORGANISM: Artificial
<220> FEATURE:
<223> OTHER INFORMATION: Primers

<400> SEQUENCE: 29
gttgaagtcc agcaggtccc tcttccgacg ttccagtgtc tgttt 45

<210> SEQ ID NO 30
<211> LENGTH: 51
<212> TYPE: DNA
<213> ORGANISM: Artificial
<220> FEATURE:
<223> OTHER INFORMATION: Primers

<400> SEQUENCE: 30
gactttctag ctgaaggagg aggcgtgcgt atcgtgggag gccaggaatg c 51

<210> SEQ ID NO 31
<211> LENGTH: 50
<212> TYPE: DNA
<213> ORGANISM: Artificial
<220> FEATURE:
<223> OTHER INFORMATION: Primers

<400> SEQUENCE: 31
cctcctcctt ctgctagaaa gtctctcttt ctgcgttcca gggtctgttt 50

<210> SEQ ID NO 32
<211> LENGTH: 42
<212> TYPE: DNA
<213> ORGANISM: Artificial
<220> FEATURE:
<223> OTHER INFORMATION: Primers

<400> SEQUENCE: 32
cctcctcctt ctgctagaaa gtccctggtc aggttgttgt cg 42

<210> SEQ ID NO 33
<211> LENGTH: 24
<212> TYPE: DNA
<213> ORGANISM: Artificial
<220> FEATURE:
<223> OTHER INFORMATION: Primers

<400> SEQUENCE: 33

-continued

```
cttgacttcg cccagacgca gcct                                        24


<210> SEQ ID NO 34
<211> LENGTH: 24
<212> TYPE: DNA
<213> ORGANISM: Artificial
<220> FEATURE:
<223> OTHER INFORMATION: Primers

<400> SEQUENCE: 34

aggctgcgtc tgggggaagt caag                                        24


<210> SEQ ID NO 35
<211> LENGTH: 26
<212> TYPE: DNA
<213> ORGANISM: Artificial
<220> FEATURE:
<223> OTHER INFORMATION: Primers

<400> SEQUENCE: 35

ggcgacaatg ctctcaccag gatcgt                                      26


<210> SEQ ID NO 36
<211> LENGTH: 27
<212> TYPE: DNA
<213> ORGANISM: Artificial
<220> FEATURE:
<223> OTHER INFORMATION: Primers

<400> SEQUENCE: 36

gatcctggtg agagcattgt cgcccct                                     27
```

SERENE PROTEASE DERIVATIVES AND USES IN THE PREVENTION OR THE TREATMENT OF BLOOD COAGULATION DISORDERS

CROSS-REFERENCE TO RELATED APPLICATIONS

This application is a continuation application of U.S. patent application Ser. No. 13/732,465 filed Jan. 2, 2013, now U.S. Pat. No. 8,518,400, which itself is a continuation application of U.S. patent application Ser. No. 13/139,367 filed Aug. 1, 2011, now U.S. Pat. No. 8,436,144 which was a 371 filing of PCT/EP2009/067632 filed Dec. 21, 2009, and the international filing claimed priority to U.S. Provisional Application 61/222,960 filed Jul. 3, 2009, European Application 09305349.4 filed Apr. 23, 2009, and European Application 08305990.7 filed Dec. 19, 2008.

FIELD OF THE INVENTION

The present invention relates to the activation peptide of factor X and its use for improving half-life and recovery of serine protease derivatives, in particular protein C, factor IX and factor X derivatives, and uses of these derivatives in the prevention or treatment of protein C, factor IX and factor X related disorders, in particular blood coagulation disorders.

BACKGROUND OF THE INVENTION

Blood coagulation is a major and complex process, which occurs in a response to blood vessel injury. It consists in a formation of clots to stop bleeding and begin repair of the damaged vessel: its wall is covered by platelets and fibrin containing clot. The process almost begins instantly after the injury.

Blood coagulation process involves two types of components: cellular components called platelets and protein components called coagulation factors. Platelets immediately form a plug at the site of injury; this is called primary haemostasis. Secondary haemostasis occurs simultaneously: proteins in the blood plasma, called coagulation factors or clotting factors, respond in a complex cascade to form fibrin strands which strengthen the platelet plug.

The coagulation cascade of secondary haemostasis is divided into two pathways called the intrinsic pathway, or contact activation pathway, and the extrinsic pathway, also called tissue factor pathway. Many coagulation factors are involved, but also cofactors and regulators, to correctly maintain the process.

For instance, Protein C is an essential factor of a major mechanism for regulating clotting, named “anticoagulant pathway”. The active form of protein C (activated protein C) is a serine protease which, when associated with another cofactor (protein S), degrades two factors of the clotting cascade essential to the massive generation of thrombin: factors Va and VIIIa. The destruction of these factors negatively regulates the amount of thrombin formed, resulting in an anticoagulant effect. This protein is particularly known to have pleiotropic biological activity: not only antithrombotic activity (Taylor et al, 1987; Gruber et al, 1990; Chesebro et al, 1992; Hanson et al, 1993; Arnljots et al, 1994; Sakamoto et al, 1994, Jang et al, 1995, Kurz et al, 1997; Gresele et al, 1998; Mizutani et al, 2000; Bernard et al 2001), but also anti-inflammatory activity (Emson, 2000), anti-apoptotic activity (Joyce et al, 2001) and pro-fibrinolytic activity (Comp et al, 1981; Rezaie, 2001).

Factor IX (hereinafter referred to as FIX) is one essential serine proteases of the blood coagulation. Deficiency of this protein causes a bleeding disorder called hemophilia B. During blood coagulation, activated FIX (FIXa) associates with its activated cofactor, factor VIIIa (hereinafter referred to as FVIIIa), converts its specific substrate factor X (FX hereinafter referred to as FX) into its activated derivative, activated factor X (hereinafter referred to as FXa).

Factor X is another essential factor of the clotting cascade. The activated form of FX (FXa) is the only serine protease which, associated with its cofactor (clotting factor Va), is capable of activating prothrombin to thrombin. Furthermore, factor X long considered a passive bystander, is now presented as a direct player on a wide variety of cell types via activation of its two main receptors, protease-activated receptor-1 (PAR-1) and PAR-2. Recent findings suggest that PAR-2 plays a crucial role in fibro-proliferative diseases such as fibrosis, tissue remodeling and cancer and point towards factor X as the important mediator coordinating the interface between coagulation and disease progression (Borensztajn et al., 2008).

The protein C, factor IX, and factor X are respectively glycoproteins of 62 kDa, 55 kDa, and 59 kDa synthesized in the liver. Before their secretion into the plasma, their polypeptide chains undergo several post-translational maturations in order to become functional proenzymes.

The two zymogens protein C and factor X are composed of an amino-terminal light chain and a carboxy-terminal heavy chain, resulting from a cleavage of peptide chain, where light and heavy chains are connected by a disulfure bridge. The zymogen factor IX is a single chain glycoprotein.

Like most serine protease precursors, protein C, factor IX, and factor X are zymogens lacking catalytic activity. Their activation is the result of proteolytic cleavage in their heavy chains. In protein C, this cleavage takes place at the N-terminal end of the heavy chain, releasing a 12 amino acid “activation” peptide. In factor X, this cleavage takes place between the Arg193 and Ile194 residues of the zymogen, also releasing an “activation” peptide, of 52 amino acids. In factor IX, two cleavages take place also releasing an activation peptide of a molecular weight approximately equal to 11 kDa from the internal region of the precursor molecule.

Blood coagulation has to be well controlled to avoid any risk of bleeding or of clotting. Thus, deregulation of blood coagulation process leads to serious disorders such as haemorrhage (increased risk of bleeding) and thrombosis (increased risk of clotting). Pathologies due to an increased risk of clotting include serious disorders such as venous or arterial thromboses, in particular thromboses affecting the large calibre vessels, myocardial infarction, thrombotic disease, pulmonary embolism, coronary reocclusions after an angioplasty or a thrombolysis, and also clotting abnormalities in patients suffering from genetic abnormalities affecting the protein C gene or that of thrombomodulin. Anticoagulants are given to people to stop thrombosis (blood clotting inappropriately presents in the blood vessels). This is useful in primary and secondary prevention of deep vein thrombosis, pulmonary embolism, myocardial infarctions and strokes in those who are predisposed. Bleeding is the most serious complication of the use of oral anticoagulation in the prevention and treatment of thromoboembolic complications. Individuals anticoagulated with warfarin or heparin are typically treated with specific antidotes such as vitamin K or protamine, respectively, if they bleed or require surgery. Unfortunately the therapeutic activities of warfarin, heparin, vitamin K, and protamine are associated with untoward side effects that complicate their use. In contrast, specific and effective antidotes are not available for the reversal of the anticoagulant effects of the low molecular weight heparins (LMWH) or the new oral anticoagulants targeting factor Xa (fXa) (see for reviews Harenberg, 2008, Bauer, 2008, Khoo et al., 2009). When these new anticoagulant therapies are used, major bleeding might be observed. Thus, prompt appropriate action, both mechanical and systemic, to control the bleeding is necessary. This includes the cessation of anticoagulation therapy and, if possible, reversal of anticoagulation effects, using available, specific reversal agents. There is currently a need for specific antidotes directed against these anticoagulants.

On the other hand, pathologies of the haemorrhagic type particularly include haemophilias A or B (deficiencies respectively in factor VIII and IX). These serious diseases are often complicated by the presence of "inhibitors" which are neutralizing allo-antibodies directed against the factor VIII or IX conventionally used for treatment.

There is currently a need for improving treatment for these pathologies.

The first strategy of treatment is to bypass the deficient steps of clotting cascade and regulation. Another strategy for improving current treatment is to improve the half-life of used compounds, mainly proteins that are easily neutralized in plasma. Another approach for improving treatment is to re-establish the auto-amplification system or retro-control.

Treatments administered for hypercoagulation disorders like protein C deficiencies are protein C, activated protein C, protein C derivatives . . . . Current treatments for haemophilias are administration of factor VIII or IX for haemophilia A and B, respectively.

These treatments are expensive, in particular because of a need for repetitive injections due to the short half-lives of compounds, and show limits, like the development of inhibitors or neutralizing allo-antibodies directed against the factor VIII or IX conventionally used for treatment of haemophilias A and B. Furthermore, it has been observed that administration of recombinant proteins, especially factor IX to treat haemophilia B, is hampered due to a lower recovery compared to the administration of plasma derived product.

Potential solutions have been proposed as new treatment strategies. Particularly, the WO03035861 patent application described thrombin-cleavable chimeric derivatives of protein C and factor X.

However, the short half-life of these compounds limits their use for blood coagulation disorders. The invention proposes a new approach to solve this technical problem.

SUMMARY OF THE INVENTION

The invention relates to a polypeptide PP comprising the amino acid sequence ranging from positions 33 to 52 of SEQ ID NO:2 (activation peptide of factor X) wherein the asparagine at position 39 or 49 is N-glycosylated.

The invention also relates to the use of said polypeptide for improving the half-life and the recovery of a circulating protein such as a serine protease zymogen, for example factor IX, factor X, protein C.

The invention also relates to a fusion protein FP comprising:

- a first polypeptide PP and
- a second polypeptide comprising the amino acid sequence ranging from positions 7 to 16 of SEQ ID NO:4.

The invention relates to a chimeric thrombin-cleavable derivative of factor X or protein C wherein the native activation peptide of said protein is replaced by a fusion protein FP.

The invention relates to thrombin-cleavable derivative of factor X or protein C wherein the native activation peptide of said protein is replaced by a fusion protein FP.

The invention further relates to a chimeric thrombin-cleavable derivative of factor X or protein C containing the activated factor X or protein C or a function conservative variant thereof and a fusion protein FP.

The invention relates to a nucleic acid molecule encoding a chimeric thrombin-cleavable derivative of the invention.

The invention relates to a chimeric derivative of factor X of the invention for use in the prevention or treatment of clotting pathologies of the haemorrhagic type.

The invention relates to a chimeric derivative of factor X of the invention for use in a method for the prevention or the treatment of bleedings induced by the low molecular weight heparins (LMWH) or by an anticoagulant targeting factor Xa (fXa).

The invention also relates to a chimeric derivative of protein C of the invention for use in the prevention or treatment of pathologies involving hypercoagulation.

The invention relates to pharmaceutical compositions for the prevention or treatment of blood coagulation disorders comprising chimeric derivatives of the invention.

DETAILED DESCRIPTION OF THE INVENTION

Working on different constructions of factor X, the inventors showed that the activation peptide of factor X plays a primordial role on the process of clearance of factor X and in its recovery.

More particularly, they observed that the nineteen amino acids of the carboxy-terminal end of this activation peptide have a major role in the kinetic of clearance of factor X. This sequence of nineteen residues contains two N-glycosylation sites essential for the observed mechanism.

DEFINITIONS

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

According to the invention, the term "fusion protein" or "chimeric protein" refers to a protein created through the joining of two or more genes or fragment thereof, which originally coded for separate polypeptides. Translation of this fusion gene results in a single polypeptide with function properties derived from each of the original polypeptides. Recombinant fusion proteins are created artificially by recombinant DNA technology for use in biological research or therapeutics. A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

The term "recovery" refers to the value expressed in percentage of an antigen or activity level of an injected molecule over a theoretical or expected antigen or activity calculated.

By "circulating protein", it is meant proteins synthesized by the cells of the body organs and transported within the blood stream. Examples of circulating proteins are blood coagulation factors, protein hormones.

The coagulation factors are generally serine proteases. There are some exceptions. For example, Factor VIII and Factor V are glycoproteins, and Factor XIII is a transglutaminase.

Protein hormones are a class of proteins that are secreted into the blood stream and have endocrine functions in living animals.

The term "serine protease zymogen" has its general meaning in the art and refers to an inactive precursor of a serine protease enzyme, which requires to be cleaved for it to become an active enzyme. According to the invention, serine proteases of interest are limited to those belonging to the circulating proteins.

Serine proteases include several proteases in which one of the amino acids at the active site is serine. According to the invention, serine proteases of interest can be, but are not limited to, factor IX, factor X or protein C, and particularly factor X and protein C.

According to the invention, the term "chimeric derivative of a serine protease zymogen" is a fusion protein obtained by the joining of a serine protease zymogen or a fragment thereof with a polypeptide of interest. Obtained protein shows the function properties of said serine protease.

Particularly, the term "chimeric derivative of a serine protease zymogen" is a fusion protein obtained by the fusion of the activated serine protease or a fragment thereof with a polypeptide of interest.

According to the invention, said chimeric derivative of a serine protease zymogen is different from the native serine protease zymogen but shows at least an equivalent activity.

The term "factor X" has its general meaning in the art and refers to a secreted serine protease implicated in coagulation mechanisms. The factor X can be from any source, but typically is a mammalian (e.g., human and non-human primate) factor X, and more particularly a human factor X. Typically, the amino acid sequence of the human factor X is provided by SEQ ID NO:1 (FIG. 1).

There are different numbering systems to localize the amino acid residues for factor X:

The system of numbering with reference of the sequence deduced from the cDNA of factor X.

The system of numbering with reference of the sequence deduced from the secreted protein, which contains the light chain, the activation peptide and the heavy chain: the amino acid residue numbered 1 is the first amino acid residue of the amino-terminal extremity of the light chain. This numbering system is used. The amino acid position upstream are negatively identifies: the C-terminal amino-acid of pro-peptide is numbered −1 and the N-terminal amino-acid residue of the translated protein (which is the amino-terminal amino acid residue of pre-peptide) is numbered −40.

As shown in FIG. 1, the sequence of factor X is divided in five different regions, which correspond, according to the used numbering system to:

the pre-peptide (or signal peptide) between the positions −40 to −28, the pro-peptide between the positions −27 to −1, the light chain between the positions 1 to 142 the activation peptide between the positions 143 to 194 the heavy chain between the position 195 to 448.

The term "Factor X" or "FX" or "mature FX" or "zymogen FX" refers to the blood circulating form of factor X, after its secretion by the producing hepatic cells. The signal peptide is cleaved off by signal peptidase, the propeptide sequence is cleaved off after gamma carboxylation took place at the first 11 glutamic acid residues at the N-terminus of the mature N-terminal chain. A further processing step occurs by cleavage between Arg142 and Ser143 according to the used numbering system (FIG. 1, positions 182-183 of SEQ ID NO:1). This processing step also leads concomitantly to the deletion of the tripeptide Arg140-Lys141-Arg142 (positions 180-182 of SEQ ID NO:1). The resulting secreted factor X zymogen consists of an N-terminal light chain of 139 amino acids and a C-terminal heavy chain of 306 amino acids which are covalently linked via a disulfide bridge between Cys132 and Cys302. Further posttranslational processing steps include the beta-hydroxylation of Asp63 as well as N- and O-type glycosylation.

The term "activated Factor X" or "FXa" refers to the enzymatically active form of circulating factor X generated in case of coagulation activity (e.g. thrombin generation) is needed. Under physiological conditions able to activate factor X, the so called activation peptide of 52 amino acids from Ser143 to Arg194 is cleaved off the rest of the molecule by cleaving carboxy-terminal end of the heavy chain at Arg194 (FIG. 1).

According to the invention, the terms "factor X" and "activated factor X" include naturally occurring factor X and activated factor X but also encompass function conservative variants and modified forms thereof. Particularly, the invention encompasses all known function-conservative variants of factor X (zymogen or activated form) such as the variant described in Camire et al, 2000, wherein the propeptide of native factor X is replaced by the propeptide of prothrombin in order to obtain a better yield of γ-carboxylated mature protein, or the variant described in Rudolph et al 1997 wherein the codon corresponding to the residue −2 of factor X (ACG, which corresponds to a threonine at position 39 of SEQ ID NO:1) can be changed in AGG (which corresponds to an arginine) to allow correct cleavage of the propeptide.

The term "activation peptide of factor X" has its general meaning in the art and refers to the 52 amino acid polypeptide ranging from the positions 143 to 194 of factor X according to the used numbering system (positions 183-234 of SEQ ID NO:1). The term may include naturally occurring factor X activation peptide and conservative function variants and modified forms thereof. The activation peptide as defined here correspond to the human activation peptide of factor X, but can be from any source, but typically is a mammalian (e.g., human and non-human primate) factor X, and more particularly a human factor X. The amino acid sequence of the human activation peptide of factor X is provided by SEQ ID NO:2.

In the invention, the 19 last amino acid sequence of the carboxy-terminal part of the activation peptide of factor X correspond to a polypeptide of interest, which correspond to amino acid sequence ranging from positions 33 to 52 of SEQ ID NO:2, or to the positions 176 to 194 of the factor X according to the used numbering system (FIG. 1). This polypeptide is also called PA176-194. This polypeptide contains two glycosylation sites at positions 39 and 49 of SEQ ID NO:2, corresponding to the positions 181 and 191 of factor X according to used numbering system.

The term "protein C" has its general meaning in the art and refers to a secreted serine protease implicated in a major mechanism of regulating clotting called "anticoagulant pathway". The protein C can be from any source, but typically is a mammalian (e.g., human and non-human primate) protein C, and more particularly a human protein C. Typically, the amino acid sequence of the human protein C is provided by SEQ ID NO:3.

The activation peptide of the protein C is a twelve amino-acids polypeptide found between the positions 200 to 211 of the sequence SED ID NO:3.

The term "Protein C" or "PC" or "mature PC" or "zymogen PC" refers to the blood circulating form of protein C, after its secretion by the hepatic producing cells. The signal peptide is cleaved off by signal peptidase, the propeptide sequence is cleaved off after gamma carboxylation took place at the first 9 glutamic acid residues at the N-terminus of the mature N-terminal chain (starting at the alanine at position 43 of the sequence SED ID NO:3). A further processing step occurs by the deletion of the doublet Lys198-Arg199 (SED ID NO:3). The resulting secreted protein C zymogen consists of an N-terminal light chain of 155 amino acids and a C-terminal heavy chain of 262 amino acids which are covalently linked via a disulfide bridge. Further posttranslational processing steps include the beta-hydroxylation of Asp113 (SED ID NO:3) as well as N-type glycosylation.

The term "activated protein X" or "PCa" refers to the enzymatically active form of circulating protein C generated in case coagulatory activity (e.g. thrombin generation) is needed. Under physiological conditions able to activate protein C, the so called activation peptide of 12 amino acids from Asp200 to Arg211 (SED ID NO:3) is cleaved off the rest of the molecule by cleaving carboxy-terminal end of the heavy chain at Arg211 (SED ID NO:3).

According to the invention, the terms "protein C" or "activated protein C" include naturally occurring protein C and activated protein C but also encompass function conservative variants and modified forms thereof. Particularly, the invention encompasses all known function-conservative variants of protein C (zymogen or activated form) such as derivatives of activated protein C with higher anticoagulant activity containing substitution at Asn 355 and 371 (U.S. Pat. No. 5,453,373) as well as derivatives of activated protein C with reduced anticoagulant activity while having the desirable property of being cytoprotective (anti-apoptotic, anti-neurodegenerative disorders and protective against stroke) (see for example WO/2005/007820). Those mutants are for instance 3K3A-APC and 229/230-APC.

The term "fibrinopeptide A" has its general meaning in the art and refers to a small peptide of 16 amino acid residues removed from the N-terminal segment of the α-chain of fibrinogen by the action of thrombin. The term may include naturally occurring fibrinopeptide A and conservative function variants and modified forms thereof. The fibrinopeptide A can be from any source, but typically is a mammalian (e.g., human and non-human primate) fibrinopeptide A, and more particularly a human fibrinopeptide A. Typically, the amino acid sequence of the human fibrinopeptide A is provided by SEQ ID NO:4.

According to the invention, the term "fibrinopeptide A thrombin-cleavable derivative" refers to a polypeptide comprising the fibrinopeptide A or a fragment thereof and a thrombin-cleavable site at the carboxy-terminal part of fibrinopeptide A. Such derivatives are defined by the sequences SEQ ID NO:5 (FIG. 3A) or SEQ ID NO:6 (FIG. 3B) for chimeric thrombin-cleavable derivatives of factor X and by the sequences SEQ ID NO:13 (FIG. 4A) or SEQ ID NO:14 (FIG. 4B) for chimeric thrombin-cleavable derivatives of protein C.

According to the invention, the term "thrombin-cleavable site" refers to a short amino acid sequence that can be recognized and cleaved by thrombin, a major serine protease of coagulation.

Glycosylation is the enzymatic process that links saccharides to proteins. Glycosylation of proteins is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Typically, the oligosaccharides that are N-linked to the proteins are composed of glucose, mannose, and 2 N-acetylglucosamine molecules which may then be elongated with a variety of different monosaccharides including galactose, N-acetylglucosamine, N-acetylgalactosamine, fucose and sialic acid.

Accordingly, the term "N-glycosylated" refers to the N-glycosylation of a polypeptide on at least one asparagine residue as defined above.

In its broadest meaning, the term "preventing" or "prevention" refers to preventing the disease or condition from occurring in a patient which has not yet been diagnosed as having it.

In its broadest meaning, the terms "treating" or "treatment" refer to reversing, alleviating, inhibiting the progress of the disorder or condition to which such term applies, or one or more symptoms of such disorder or condition.

The term "patient" refers to any subject (preferably human) afflicted with or susceptible to be afflicted with a blood coagulation disorder.

According to the invention, the term "protein C and factor X related disorders" refers to any pathology involving factor X or protein C, in particular blood coagulation disorders.

According to the invention, the term "blood coagulation disorder" or "clotting disorder" refers to any pathology due to a deregulation of blood coagulation mechanisms. It thus includes pathologies involving an excess and a default in blood coagulation.

Pathologies involving an excess of blood coagulation, or a hypercoagulation, include, but are not limited to venous or arterial thromboses, myocardial infarction, thrombotic disease, pulmonary embolism, coronary reocclusions, and deficiency in protein C.

Pathologies involving a default of blood coagulation are called haemorrhagic pathologies and particularly include factor VIII, IX or XI deficiencies. These pathologies may in particular be haemophilias A or B and haemophilias resulting from the appearance of auto-antibodies associated with another pathology such as autoimmune disease or cancer.

Polypeptides Derived from the Activation Peptide of Factor X

A first object of the present invention relates to a polypeptide PP comprising the amino acid sequence ranging from positions 33 to 52 of SEQ ID NO:2 wherein the asparagine at position 39 or 49 is N-glycosylated.

In a preferred embodiment, the asparagines at positions 39 and 49 are N-glycosylated.

In one embodiment, said polypeptide comprises the amino acid sequence ranging from positions 33 to 52 of SEQ ID NO:2.

In a particular embodiment, said polypeptide comprises the amino acid sequence ranging from positions 32 to 52 of SEQ ID NO:2.

In a particular embodiment, said polypeptide comprises the amino acid sequence ranging from positions 31 to 52 of SEQ ID NO:2.

In a particular embodiment, said polypeptide comprises the amino acid sequence ranging from positions 30 to 52 of SEQ ID NO:2.

In a particular embodiment, said polypeptide comprises the amino acid sequence ranging from positions 29 to 52 of SEQ ID NO:2.

In a particular embodiment, said polypeptide comprises the amino acid sequence ranging from positions 28 to 52 of SEQ ID NO:2.

In a particular embodiment, said polypeptide comprises the amino acid sequence ranging from positions 27 to 52 of SEQ ID NO:2.

In a particular embodiment, said polypeptide comprises the amino acid sequence ranging from positions 26 to 52 of SEQ ID NO:2.

In a particular embodiment, said polypeptide comprises the amino acid sequence ranging from positions 25 to 52 of SEQ ID NO:2.

In a particular embodiment, said polypeptide comprises the amino acid sequence ranging from positions 24 to 52 of SEQ ID NO:2.

In a particular embodiment, said polypeptide comprises the amino acid sequence ranging from positions 23 to 52 of SEQ ID NO:2.

In a particular embodiment, said polypeptide comprises the amino acid sequence ranging from positions 22 to 52 of SEQ ID NO:2.

In a particular embodiment, said polypeptide comprises the amino acid sequence ranging from positions 21 to 52 of SEQ ID NO:2.

In a particular embodiment, said polypeptide comprises the amino acid sequence ranging from positions 20 to 52 of SEQ ID NO:2.

In a particular embodiment, said polypeptide comprises the amino acid sequence ranging from positions 19 to 52 of SEQ ID NO:2.

In a particular embodiment, said polypeptide comprises the amino acid sequence ranging from positions 18 to 52 of SEQ ID NO:2.

In a particular embodiment, said polypeptide comprises the amino acid sequence ranging from positions 17 to 52 of SEQ ID NO:2.

In a particular embodiment, said polypeptide comprises the amino acid sequence ranging from positions 16 to 52 of SEQ ID NO:2.

In a particular embodiment, said polypeptide comprises the amino acid sequence ranging from positions 15 to 52 of SEQ ID NO:2.

In a particular embodiment, said polypeptide comprises the amino acid sequence ranging from positions 14 to 52 of SEQ ID NO:2.

In a particular embodiment, said polypeptide comprises the amino acid sequence ranging from positions 13 to 52 of SEQ ID NO:2.

In a particular embodiment, said polypeptide comprises the amino acid sequence ranging from positions 12 to 52 of SEQ ID NO:2.

In a particular embodiment, said polypeptide comprises the amino acid sequence ranging from positions 11 to 52 of SEQ ID NO:2.

In a particular embodiment, said polypeptide comprises the amino acid sequence ranging from positions 10 to 52 of SEQ ID NO:2.

In a particular embodiment, said polypeptide comprises the amino acid sequence ranging from positions 9 to 52 of SEQ ID NO:2.

In a particular embodiment, said polypeptide comprises the amino acid sequence ranging from positions 8 to 52 of SEQ ID NO:2.

In a particular embodiment, said polypeptide comprises the amino acid sequence ranging from positions 7 to 52 of SEQ ID NO:2.

In a particular embodiment, said polypeptide comprises the amino acid sequence ranging from positions 6 to 52 of SEQ ID NO:2.

In a particular embodiment, said polypeptide comprises the amino acid sequence ranging from positions 5 to 52 of SEQ ID NO:2.

In a particular embodiment, said polypeptide comprises the amino acid sequence ranging from positions 4 to 52 of SEQ ID NO:2.

In a particular embodiment, said polypeptide comprises the amino acid sequence ranging from positions 3 to 52 of SEQ ID NO:2.

In a particular embodiment, said polypeptide comprises the amino acid sequence ranging from positions 2 to 52 of SEQ ID NO:2.

In a particular embodiment, said polypeptide comprises the amino acid sequence SEQ ID NO:2. In an alternative embodiment, said polypeptide does not comprise the amino acid sequence SEQ ID NO:2.

Another object of the present invention relates to the use of a polypeptide PP for improving the half-life of a zymogen, particularly the half-life of a serine protease zymogen.

Fusion Proteins Derived from the Activation Peptide of Factor X

A further object of the invention relates to a fusion protein FP comprising:

- a first polypeptide consisting of a polypeptide PP as described above and
- a second polypeptide comprising the amino acid sequence ranging from positions 7 to 16 of SEQ ID NO:4.

A further object of the invention relates to a fusion protein

FP comprising:

a first polypeptide consisting of a polypeptide PP as described above and a second polypeptide comprising the amino acid sequence ranging from positions 7 to 16 of SEQ ID NO:4, wherein the glycine corresponding to the residue at position 14 of SEQ ID NO:4 is replaced by a valine, a phenylalanine or an alanine and/or the valine corresponding to the residue at position 15 of SEQ ID NO:4 is replaced by a proline.

In a preferred embodiment, the invention relates to said fusion proteins wherein the carboxy-terminal region of the first polypeptide is fused to the amino-terminal region of the second polypeptide.

In a particular embodiment, said second polypeptide comprises the amino acid sequence ranging from positions 7 to 16 of SEQ ID NO:4.

In another particular embodiment, said second polypeptide comprises the amino acid sequence ranging from positions 6 to 16 of SEQ ID NO:4.

In another particular embodiment, said second polypeptide comprises the amino acid sequence ranging from positions 5 to 16 of SEQ ID NO:4.

In another particular embodiment, said second polypeptide comprises the amino acid sequence ranging from positions 4 to 16 of SEQ ID NO:4.

In another particular embodiment, said second polypeptide comprises the amino acid sequence ranging from positions 3 to 16 of SEQ ID NO:4.

In another particular embodiment, said second polypeptide comprises the amino acid sequence ranging from positions 2 to 16 of SEQ ID NO:4.

In another particular embodiment, said second polypeptide comprises the amino acid sequence SEQ ID NO:4.

Chimeric Derivatives of the Invention

Polypeptides and fusion proteins of the invention as described above can be fused to serine protease zymogen or active form, or fragment thereof, to improve the half-life and the recovery of said serine protease zymogen.

The inventors have shown that the activation peptide of factor X and more particularly a fragment thereof containing the nineteen last amino acids of it has a major role in the long half-life of factor X and a good recovery of the injected molecule. They also showed that the activation peptide of factor X or a fragment thereof containing the nineteen last amino acids of it can be used to increase the half-life and the recovery of other proteins, such as circulating proteins.

Thus, a further object of the invention relates to a chimeric protein containing a protein of interest and a polypeptide PP as described above.

Said protein of interest can be an enzyme or other protein which has a short half-life in blood. Particularly, it can be a circulating protein, such as a serine protease or a protein hormone.

Typically, said protein of interest can be protein C, factor VII, activated factor VII, factor IX, insulin, erythropoietin, soluble P-selectin glycoprotein ligand . . . but is not the native factor X.

Said protein can be used in its zymogen form or in its activated form.

In a particular embodiment, the invention relates to said protein in that the polypeptide PP is fused to the protein of interest at the carboxy-terminal end, the amino-terminal end or into the amino acid sequence of the protein of interest.

In a particular embodiment, the invention relates to said chimeric protein in that the polypeptide PP is fused to the protein of interest in the carboxy-terminal end, the amino-terminal end or into the amino acid sequence of the protein of interest.

In a particular embodiment, the invention relates to said chimeric protein in that the activation peptide of the zymogen of interest is replaced by a polypeptide PP.

In another particular embodiment, the invention relates to said chimeric protein in that said polypeptide PP is fused to the activated form of the protein of interest at the location site of its native activation peptide.

In a particular embodiment, the invention relates to said chimeric protein in that the polypeptide PP consists of the amino acid sequence ranging from positions 33 to 52 of SEQ ID NO:2 wherein the asparagine at position 39 or 49 is N-glycosylated.

Typically, the invention relates to said chimeric protein wherein said polypeptide PP comprises the amino acid sequence ranging from positions 33 to 52 of SEQ ID NO:2 wherein the asparagine at position 39 or 49 is N-glycosylated and has a maximal length of 19 amino acids, 20, 25, 30, 35, 40, 45 or 50 amino acids.

In a particular embodiment, the invention relates to said chimeric protein in that the polypeptide PP does not consist of the native active peptide of factor X (SEQ ID NO:2).

In a particular embodiment, the invention relates to said chimeric protein which is not one of proteins described in the patent application WO2006018204.

In a particular embodiment, the invention relates to a chimeric protein comprising the protein C and a polypeptide PP, provided that the sequence of said peptide does not consists of the amino acid sequence SEQ ID NO:2.

In a more particular embodiment, the invention relates to a chimeric protein comprising the protein C and a polypeptide PP wherein said polypeptide consists of the amino acid sequence ranging from positions 33 to 52 of SEQ ID NO:2 wherein the asparagine at position 39 or 49 is N-glycosylated.

In a particular embodiment, the invention relates to a chimeric protein comprising the protein C wherein the activation peptide of protein C is replaced by a polypeptide PP, provided that the sequence of said peptide does not consists of the amino acid sequence SEQ ID NO:2.

In a more particular embodiment, the invention relates to a chimeric protein comprising the protein C wherein the activation peptide of protein C is replaced by a polypeptide PP consisting of the amino acid sequence ranging from positions 33 to 52 of SEQ ID NO:2 wherein the asparagine at position 39 or 49 is N-glycosylated.

In a particular embodiment, the invention relates to a chimeric protein comprising the activated protein C and a polypeptide PP, provided that the sequence of said peptide does not consists of the amino acid sequence SEQ ID NO:2.

In a more particular embodiment, the invention relates to a chimeric protein comprising the activated protein C and a polypeptide PP consisting of the amino acid sequence ranging from positions 33 to 52 of SEQ ID NO:2 wherein the asparagine at position 39 or 49 is N-glycosylated.

Preferably, the amino acid sequence ranging from positions 33 to 52 of SEQ ID NO:2 wherein the asparagine at position 39 or 49 is N-glycosylated is fusion on the N-terminal part of the heavy chain of activated protein C.

The present invention relates to a chimeric derivative of a serine protease zymogen comprising a polypeptide PP.

Particularly, said chimeric derivatives of serine protease zymogen are chimeric derivatives of protein C and factor X. In particular, chimeric thrombin-cleavable derivatives described in the WO03035861 patent application or in Louvain-Quintard et al., 2005, are used and modified.

The invention thus relates to a chimeric thrombin-cleavable derivative of factor X wherein the native activation peptide of said protein is replaced by a fusion protein FP as described above.

According to the invention, the invention also encompasses the function conservative variants of chimeric thrombin-cleavable derivatives of factor X of the invention.

In a particular embodiment, the invention further relates to a chimeric thrombin-cleavable derivative of factor X wherein the amino acids corresponding to the three first residues of the heavy chain of native factor X (Ile-Val-Gly, positions 235-237 of SEQ ID NO:1) can be modified according to the modifications described in Toso R and al, 2008 and the patent applications WO03035861 and WO04005347.

Particularly, the invention relates to said chimeric thrombin-cleavable derivative of factor X wherein:

the isoleucine corresponding to the residue at position 235 of SEQ ID NO:1 can be replaced by an alanine, a serine or a leucine;

the valine corresponding to the residue at position 236 of SEQ ID NO:1 can be replaced by a phenylalanine or an alanine.

In another particular embodiment, the invention further relates to a chimeric thrombin-cleavable derivative of factor X wherein the amino acids corresponding to the three last residues of the fibrinopeptide A (Gly-Val-Arg, positions 14-16 of SEQ ID NO:4) can also be modified according to the modifications described in Gustafsson D and al, 2004 and the patent application WO04005347.

Particularly, the invention relates to said chimeric thrombin-cleavable derivative of factor X wherein:

the glycine corresponding to the residue at position 14 of SEQ ID NO:4 can be replaced by a valine, a phenylalanine or an alanine, the valine corresponding to the residue at position 15 of SEQ ID NO:4 can be replaced by a proline.

According to the invention, said modifications are used to improve the cleavage by thrombin or the efficacy of the activated factor X derivative and do not alter the activity of the chimeric thrombin-cleavable derivatives of the invention.

Accordingly, the invention relates to a chimeric thrombin-cleavable derivative of factor X wherein the native activation peptide of said protein is replaced by a fusion protein comprising:

a polypeptide PP and a fibrinopeptide A thrombin-cleavable derivative defined by the amino acid sequence SEQ ID NO:5 or SEQ ID NO:6.

In one embodiment, said chimeric thrombin cleavable derivative of factor X is characterised in that said polypeptide is the native activation peptide of factor X (SEQ ID NO:2).

In another embodiment, said chimeric thrombin cleavable derivative of factor X is characterised in that said fibrinopeptide A thrombin-cleavable derivative is defined by a amino acid sequence selected by a amino acid sequence selected for the group of SEQ ID NO:7, SEQ ID NO:8, SEQ ID NO:9, SEQ ID NO:10, SEQ ID NO:11 and SEQ ID NO:12.

In a particular embodiment, the invention relates to said chimeric thrombin-cleavable derivative of factor X wherein:

said polypeptide is the native activation peptide of factor X (SEQ ID NO:2) and said fibrinopeptide A thrombin-cleavable derivative is defined by the amino acid sequence DFLAEGGGVRIVG (SEQ ID NO:7).

The invention also relates to a chimeric thrombin-cleavable derivative of protein C wherein in that the native activation peptide of said protein is replaced by a fusion protein FP.

According to the invention, the invention also encompasses the function conservative variants of chimeric thrombin-cleavable derivatives of protein C of the invention.

In a particular embodiment, in said chimeric thrombin-cleavable derivatives of protein C, the amino acids corresponding to the three first residues of the heavy chain of native protein C (Leu-Ile-Asp, positions 212-214 of SEQ ID NO:3) can be modified according to the modifications described in the patent application WO03035861.

Particularly, in the chimeric thrombin-cleavable derivative of protein C of the invention:

the leucine corresponding to the residue at position 212 of SEQ ID NO:3 can be replaced by an alanine or a serine;

the isoleucine corresponding to the residue at position 213 of SEQ ID NO:3 can be replaced by a phenylalanine;

the aspartate corresponding to the residue at position 214 of SEQ ID NO:3 can be replaced by a glycine.

In another particular embodiment, the invention further relates to a chimeric thrombin-cleavable derivative of protein C wherein the amino acids corresponding to the three last residues of the fibrinopeptide A (Gly-Val-Arg, positions 14-16 of SEQ ID NO:4) can also be modified according to the modifications described in Gustafsson D and al, 2004 and the patent application WO04005347.

Particularly, the invention relates to said chimeric thrombin-cleavable derivative of factor X wherein:

the glycine corresponding to the residue at position 14 of SEQ ID NO:4 can be replaced by a valine, a phenylalanine or an alanine, the valine corresponding to the residue at position 15 of SEQ ID NO:4 can be replaced by a proline.

According to the invention, said modifications are used to improve the cleavage by thrombin or the efficacy of the activated protein C derivative and do not alter the activity of the chimeric thrombin-cleavable derivatives of the invention.

The invention also relates to a chimeric thrombin-cleavable derivative of protein C wherein the native activation peptide of said protein is replaced by a fusion protein comprising:

a polypeptide PP and a fibrinopeptide A thrombin-cleavable derivative defined by the amino acid sequence SEQ ID NO:13 or SEQ ID NO:14.

In one embodiment, said polypeptide is the native activation peptide of factor X (SEQ ID NO:2).

In another embodiment, said fibrinopeptide A thrombin-cleavable derivative is defined by a amino acid sequence selected by a amino acid sequence selected for the group of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26.

In a particular embodiment, the invention relates to said chimeric thrombin-cleavable derivative of protein C wherein:

said polypeptide is the native activation peptide of factor X (SEQ ID NO:2) and said fibrinopeptide A thrombin-cleavable derivative is defined by the amino acid sequence DFLAEGGGVRLID (SEQ ID NO:15).

A further object of the invention relates to a chimeric derivative of protein C wherein a polypeptide PP is fused at the amino-terminal part of the activation peptide of native protein C.

A further object of the invention relates to a chimeric derivative of a serine protease zymogen characterised in that it contains said activated serine protease or a function conservative variant thereof and a polypeptide PP.

Particularly, the invention relates to a chimeric thrombin-cleavable derivative of a serine protease of interest characterised in that it contains said activated serine protease or a function conservative variant thereof and a fusion protein FP.

In a particular embodiment, the invention relates to a chimeric thrombin-cleavable derivative of factor X containing the activated factor X or a function conservative variant thereof and a fusion protein FP.

In a preferred embodiment, the invention relates to a chimeric thrombin-cleavable derivative of factor X containing the activated factor X or a function conservative variant thereof and a fusion protein FP wherein the carboxy-terminal part of the fusion protein FP is fused to the amino-terminal part of the heavy chain of activated factor X.

According to the invention, some amino acids can be substituted, deleted or added to improve the activity of the chimeric thrombin-cleavable derivative of factor X of the invention. Particularly, the amino acids corresponding to the three last amino acids of fibrinopeptide A (positions 14 to 16 of the amino acid sequence SEQ ID NO:4) and the three first amino acids of the heavy chain of the activated factor X (positions 235 to 237 of the amino acid sequence SEQ ID NO:1) can be modified as detailed above.

Particularly, the invention relates to said chimeric thrombin-cleavable derivative of factor X of the invention wherein:

the isoleucine corresponding to the residue at position 235 of SEQ ID NO:1 can be replaced by an alanine, a serine or a leucine;

the valine corresponding to the residue at position 236 of SEQ ID NO:1 can be replaced by a phenylalanine or an alanine.

the glycine corresponding to the residue at position 14 of SEQ ID NO:4 can be replaced by a valine, a phenylalanine or an alanine, the valine corresponding to the residue at position 15 of SEQ ID NO:4 can be replaced by a proline, According to the invention, said modifications are used to improve the cleavage by thrombin or the efficacy of the activated factor X derivative and do not alter the activity of the chimeric thrombin-cleavable derivatives of the invention.

In a particular embodiment, the invention relates to a chimeric thrombin-cleavable derivative of protein C containing the activated protein C or a function conservative variant thereof and a fusion protein FP.

In a preferred embodiment, the invention relates to a chimeric thrombin-cleavable derivative of protein C containing the activated protein C or a function conservative variant thereof and a fusion protein FP wherein the carboxy-terminal part of the fusion protein FP is fused to the amino-terminal part of the heavy chain of activated protein C.

According to the invention, some amino acids can be substituted, deleted or added to improve the chimeric thrombin-cleavable derivative of protein C of the invention. Particularly, the amino acids corresponding to the three first amino acids of the heavy chain of the activated protein C (positions 212-214 of SEQ ID NO:3) can be modified as detailed above.

Particularly, in the chimeric thrombin-cleavable derivative of protein C of the invention:

the leucine corresponding to the residue at position 212 of SEQ ID NO:3 can be replaced by an alanine or a serine;

the isoleucine corresponding to the residue at position 213 of SEQ ID NO:3 can be replaced by a phenylalanine;

the aspartate corresponding to the residue at position 214 of SEQ ID NO:3 can be replaced by a glycine;

the glycine corresponding to the residue at position 14 of SEQ ID NO:4 can be replaced by a valine, a phenylalanine or an alanine;

the valine corresponding to the residue at position 15 of SEQ ID NO:4 can be replaced by a proline.

According to the invention, said modifications are used to improve the cleavage by thrombin or the efficacy of the activated protein C derivative and do not alter the activity of the chimeric thrombin-cleavable derivatives of the invention.

Nucleic Acids, Vectors and Recombinant Host Cells

A further object of the present invention relates to a nucleic acid molecule encoding polypeptides and chimeric derivatives according to the invention.

In one embodiment, the invention relates to a nucleic acid molecule encoding a chimeric thrombin-cleavable derivative of factor X as described above.

In another embodiment, the invention relates to a nucleic acid molecule encoding a chimeric thrombin-cleavable derivative of protein C as described above.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid molecules can be obtained by conventional methods well known to those skilled in the art, in particular by site-directed mutagenesis of the gene encoding the native protein.

Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Any expression vector for animal cell can be used, so long as a gene encoding a polypeptide or chimeric derivative of the invention can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The invention also includes gene delivery systems comprising a nucleic acid molecule of the invention, which can be used in gene therapy in vivo or ex vivo. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

A subject of the present invention is also a prokaryotic or eukaryotic host cell genetically transformed with at least one nucleic acid molecule according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

Preferably, for expressing and producing the polypeptides and chimeric derivatives, and in particular the protein C and factor X derivatives in accordance with the invention, eukaryotic cells, in particular mammalian cells, and more particularly human cells, will be chosen.

Typically, cell lines such as CHO, BHK-21, COS-7, C127, PER.C6 or HEK293 could be used, for their ability to process to the right post-translational modifications of the derivatives.

The present invention also encompasses transgenic animals, in particular transgenic non-human mammals hosting at least a transgene comprising an expression cassette of the invention. Said transgenic animals can be used for producing chimeric proteins of the invention, as already described for instance by Brink et al., 2000.

The construction of expression vectors in accordance with the invention, the transformation of the host cells, and the production of transgenic animals can be carried out using conventional molecular biology techniques. The chimeric derivatives of the invention, and in particular the protein C or factor X derivatives, can, for example, be obtained by culturing genetically transformed cells in accordance with the invention and recovering the derivative expressed by said cell, from the culture. They may then, if necessary, be purified by conventional procedures, known in themselves to those skilled in the art, for example by fractionated precipitation, in particular ammonium sulphate precipitation, electrophoresis, gel filtration, affinity chromatography, etc.

In particular, conventional methods for preparing and purifying recombinant proteins may be used for producing the proteins in accordance with the invention. For example, for producing the protein C derivatives in accordance with the invention, methods such as those described in U.S. Pat. No. 4,992,373 or U.S. Pat. No. 4,981,952 may be used.

Therapeutic Methods and Uses

A third object of the invention relates to a chimeric derivative according to the invention for use in the prevention or treatment of protein C and factor X related disorders, in particular blood coagulation disorders.

In one embodiment, the invention relates to a chimeric derivative of factor X of the invention as a pro-coagulant agent.

In a particular embodiment, the invention relates to a chimeric derivative of factor X for use in the prevention or treatment of clotting pathologies of the haemorrhagic type, in particular ensuing from a factor VIII, IX or XI deficiency.

These pathologies may in particular be haemophilias A or B, which may or may not be complicated by the presence of inhibitors (neutralizing allo-antibodies directed against the factor VIII or IX conventionally used for treatment); they may also be acquired haemophilias resulting from the appearance of auto antibodies associated with another pathology (autoimmune disease, cancer, lymphoproliferative syndrome, idiopathic disorder, etc.).

In a particular embodiment, the invention relates to a chimeric derivative of factor X for use in the prevention or treatment of haemophilias A or B.

In another embodiment, the invention relates to a chimeric derivative of factor IX for use in the prevention or treatment of haemophilia B.

In another embodiment, the invention relates to a chimeric derivative of factor X for use in the prevention or treatment of fibroproliferative diseases such as fibrosis tissue remodelling and cancer.

The invention relates to a chimeric derivative of factor X of the invention for use in a method for the prevention or the treatment of bleedings induced by the low molecular weight heparins (LMWH) or by an anticoagulant targeting factor Xa (fXa).

Anticoagulant targeting factor Xa are well known (see for reviews Harenberg, 2008, Bauer, 2008, Khoo et al., 2009). Examples of anticoagulants targeting factor Xa are rivaroxaban and betrixaban.

In a preferred embodiment the serine of said chimeric derivative of factor X corresponding to the residue at position 419 of SEQ ID NO:1 is replaced by an alanine.

In another embodiment arginine, lysine and serine of said chimeric derivative of factor X corresponding respectively to residues at position 387, 391, and 419 of SEQ ID NO:1 are replaced by an alanine.

These chimeric derivatives of factor X of the invention have been modified such that they bind, either directly or indirectly, to a factor Xa inhibitor.

Structurally, these derivatives are modified to provide either no procoagulant activity or reduced procoagulant activity and do not assemble into the prothrombinase complex for the latter embodiment.

In another embodiment, the invention relates to a chimeric derivative of protein C as an antithrombotic, anti-inflammatory, anti-neurodegeneration and anti-apoptotic agent.

In a particular embodiment, the invention relates to a chimeric derivative of protein C for use in the prevention or treatment of pathologies involving hypercoagulation.

Such pathologies include, but are not limited to venous or arterial thromboses, in particular thromboses affecting the large calibre vessels, myocardial infarction, thrombotic disease, pulmonary embolism, coronary reocclusions after an angioplasty or a thrombolysis, stroke, and also clotting abnormalities in patients suffering from genetic abnormalities affecting the PC gene or that of thrombomodulin.

In a particular embodiment, the invention relates to a chimeric derivative of protein C for use in the prevention or treatment of haemophilias A or B.

In another embodiment, the invention relates to a chimeric derivative of protein C for use in the prevention or treatment of respiratory and inflammatory diseases.

Preferably, said chimeric derivative is administered in a therapeutically effective amount.

By a "therapeutically effective amount" is meant a sufficient amount of the chimeric derivative of the invention to treat or to prevent protein C and factor X related disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Pharmaceutical Compositions

A further object of the invention relates to pharmaceutical compositions comprising chimeric derivatives of the invention for the prevention or treatment of protein C and factor X related disorders, in particular blood coagulation disorders.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In one embodiment, the invention relates to pharmaceutical compositions comprising a chimeric derivative of factor X for the treatment of clotting pathologies of the haemorrhagic type, fibroproliferative as detailed above.

In another embodiment, the invention relates to pharmaceutical compositions comprising a chimeric derivative of protein C for the prevention or treatment of pathologies involving hypercoagulation, inflammatory or respiratory diseases, as detailed above.

The chimeric derivatives of serine protease zymogen may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The chimeric derivatives of serine protease zymogen of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The chimeric derivatives of serine protease zymogen of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

FIGURES

FIG. 1: Schematic representation of different parts of factor X zymogen amino acid sequence.

The pre-peptide (or signal peptide) is defined by the amino acid sequence between the positions −40 to −18 and the pro-peptide by the amino acid sequence between the positions −17 to −1. The light chain corresponds to the sequence between the amino acid positions 1 to 142 and the heavy chain between amino acid positions 195 to 448. The activation peptide (positions 143 to 194) is boxed and N-glycosylation sites of interest are tagged by an *. The numbering system used appears on the same line as the sequence and the other reference system appears in grey on the line under the sequence.

FIG. 2: Schematic representation of fibrinopeptide A thrombin-cleavable derivatives for thrombin-cleavable derivatives of factor X.

A. Said fibrinopeptide A thrombin-cleavable derivatives contain the amino acid sequence of fibrinopeptide A, wherein the amino acids in positions 14 or 15 can be modified according to the figure. At the carboxy-terminal part, 3 more amino acids are added to form a thrombin-cleavable site of 6 amino acids with the 3 last amino acids of fibrinopeptide A (or derivative).

B. In a preferred mode of the invention, only the 10 last amino acids of fibrinopeptide A are used and fused with a 3 amino acids peptide to form a thrombin cleavable site.

FIG. 3: Schematic representation of fibrinopeptide A thrombin-cleavable derivatives for thrombin-cleavable derivatives of protein C.

A. Said fibrinopeptide A thrombin-cleavable derivatives contain the amino acid sequence of fibrinopeptide A and 3 amino acids are added at the carboxy-terminal part to form a thrombin-cleavable site of 6 amino acids with the 3 last amino acids of fibrinopeptide A (or derivative).

B. In a preferred mode of the invention, only the 10 last amino acids of fibrinopeptide A are used and fused with a 3 amino acids peptide to form a thrombin cleavable site.

FIG. 4: Schematic representation of FX variant constructs.

There are seven recombinant Factor X (FX) proteins. The protein domains are as follows: in grey the light chain, in white the activation peptide (AP) and in black the catalytic domain of Factor X. The activation peptide is the site of differences between the different variants. FpA corresponds to the fibrinopeptide A thrombin-cleavable derivative defined by SEQ ID NO:7, ap to the residues 176-194 of the carboxy-terminal end of FX activation peptide, and black lines indicate the site of mutations N181A and N191A in the FX activation peptide.

Figure 5:
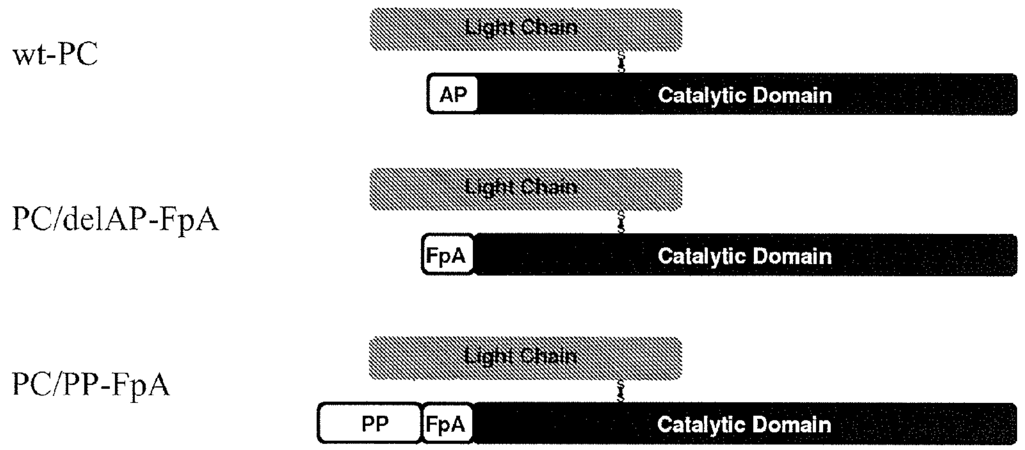

FIG. 5: Schematic representation of protein C variant constructs.

There are three recombinant protein C proteins. The protein domains are as follows: in grey the light chain, in white the activation peptide (AP) and in black the catalytic domain of protein C. FpA corresponds to the fibrinopeptide A thrombin-cleavable derivative defined by SEQ ID NO:7, PP to the residues 176-194 of the carboxyterminal end of FX activation peptide.

Figure 6:
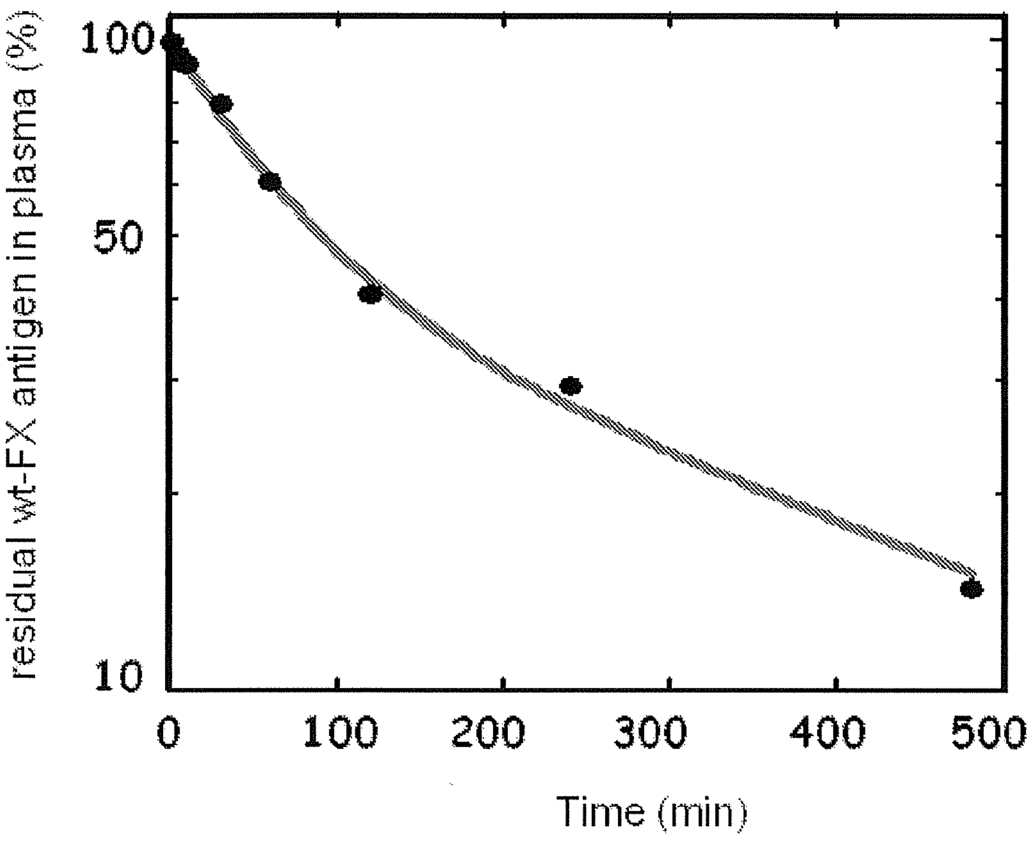

FIG. 6: Biphasic clearance of wt-FX from plasma.

Mice were injected intravenously with purified wt-FX (10 μg/mouse). At indicated time points blood sample were taken. The amount of residual wt-FX antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

Figure 7:
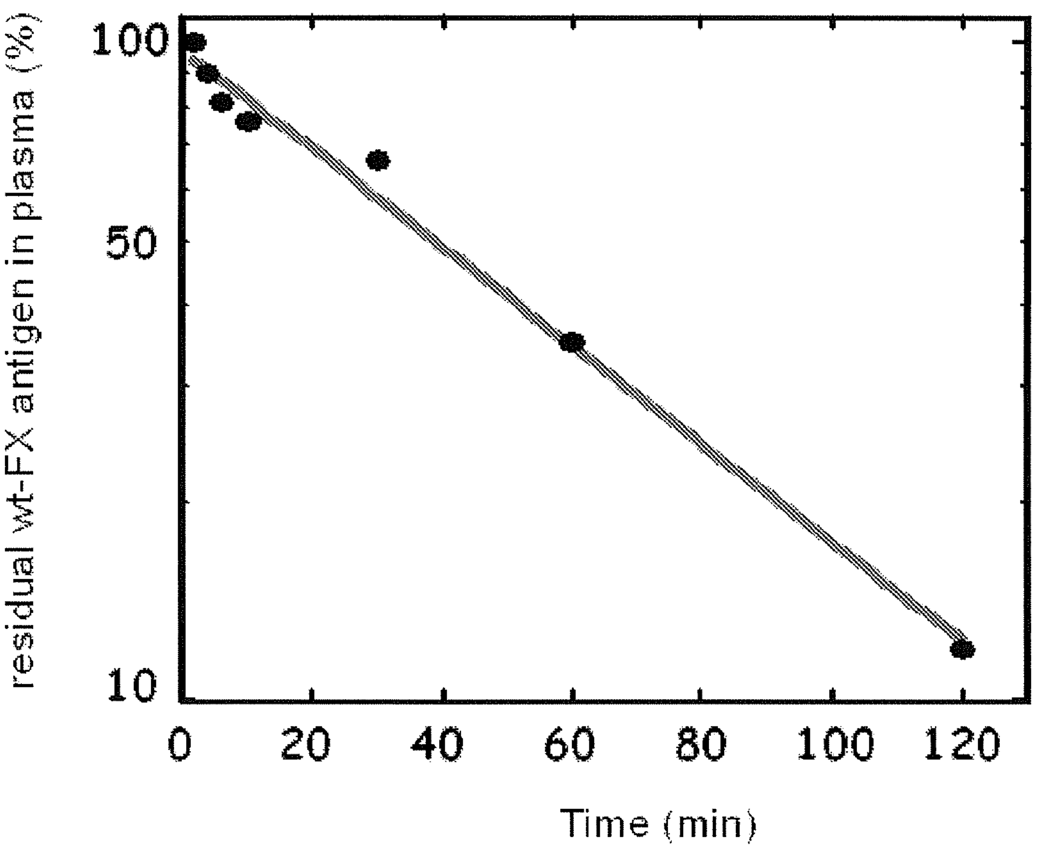

FIG. 7: Monophasic clearance of FX/delAP-FpA from plasma.

Mice were injected intravenously with purified FX/delAP-FpA (10 μg/mouse). At indicated time points blood sample were taken. The amount of residual FX/delAP-FpA antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

Figure 8:
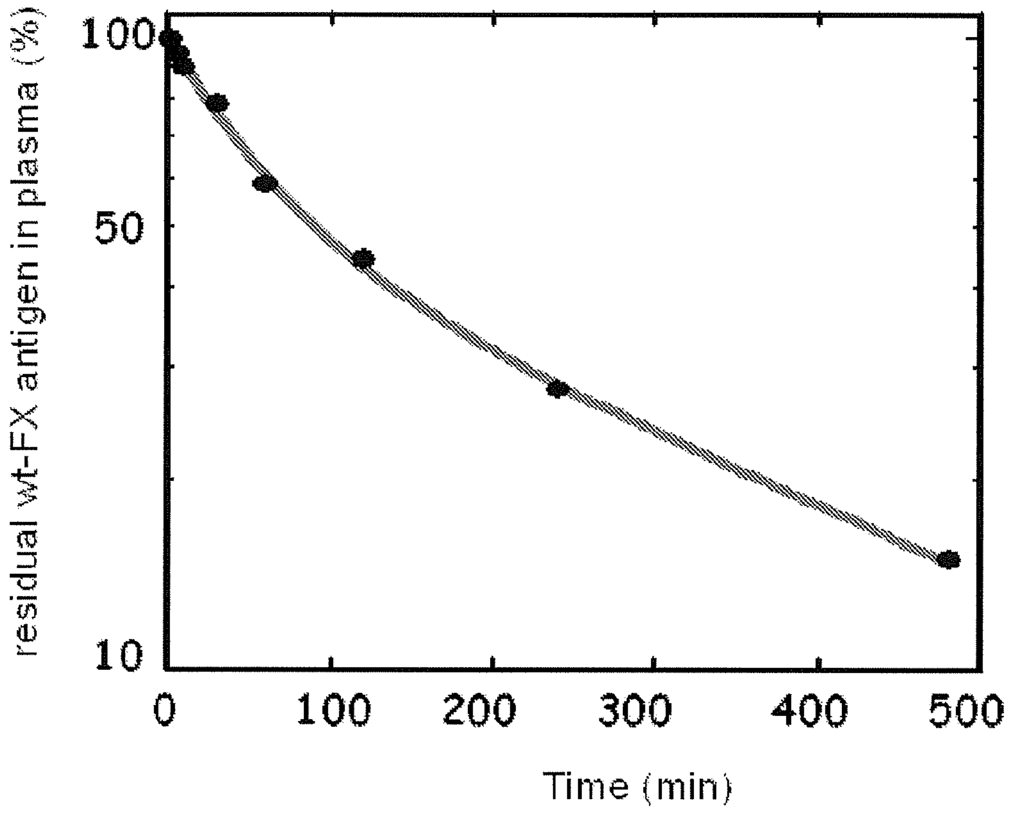

FIG. 8: Biphasic clearance of FX/AP-FpA from plasma.

Mice were injected intravenously with purified FX/AP-FpA (10 μg/mouse). At indicated time points blood sample were taken. The amount of residual FX/AP-FpA antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

Figure 9:
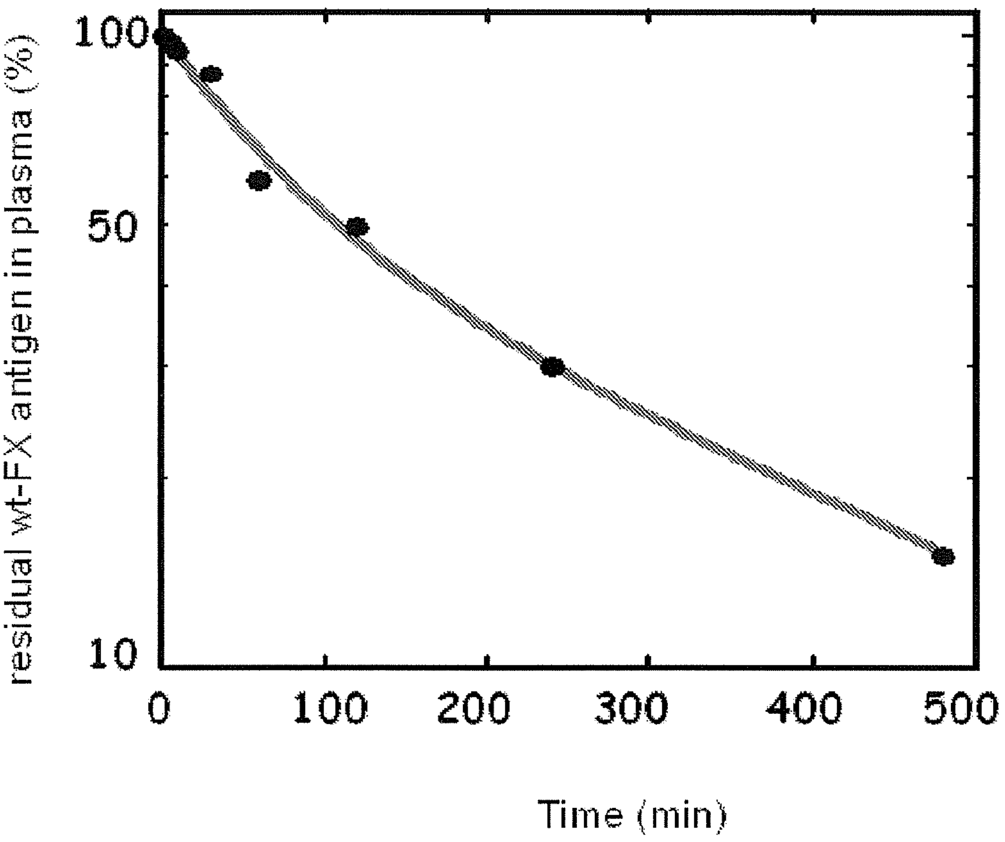

FIG. 9: Biphasic clearance of FX/AP176-194 from plasma.

Mice were injected intravenously with purified FX/AP176-194 (10 μg/mouse). At indicated time points blood sample were taken. The amount of residual FX/AP176-194 antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

Figure 10:
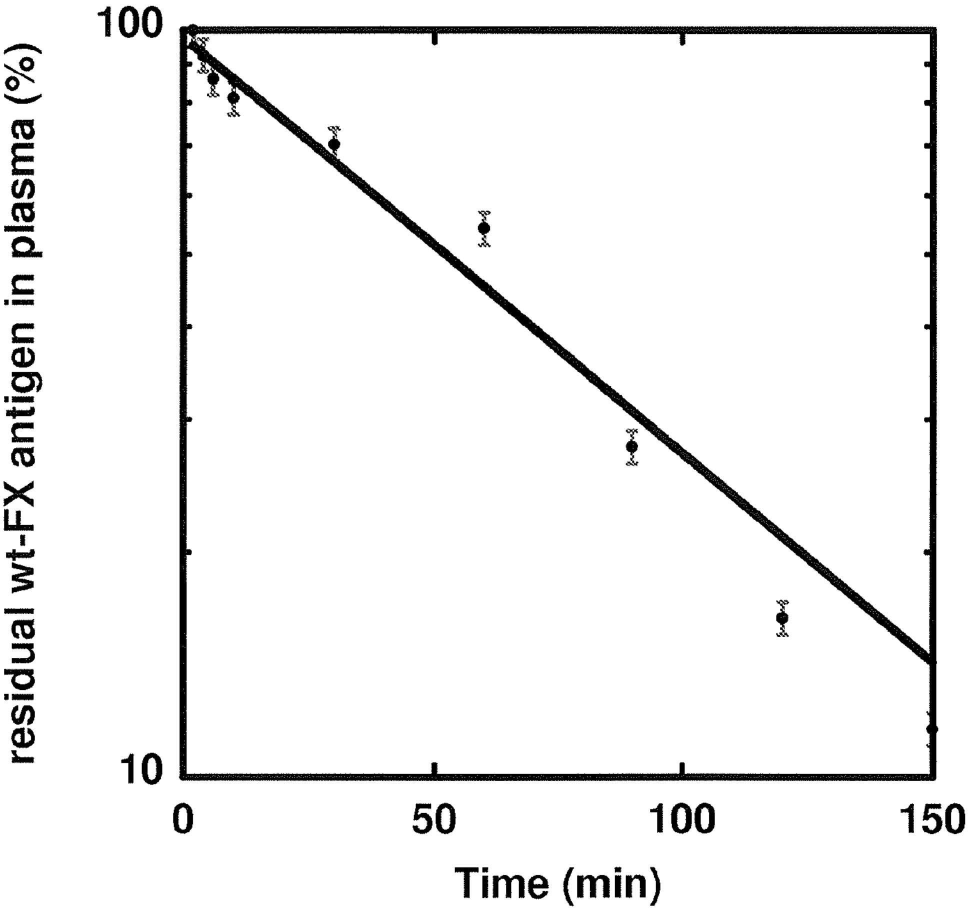

FIG. 10: Monophasic clearance of FX/AP176-194-N181A-N191A from plasma.

Mice were injected intravenously with purified FX/AP176-194-N181A-N191A (10 μg/mouse). At indicated time points blood sample were taken. The amount of residual FX/AP176-194-N181A-N191A antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

Figure 11:
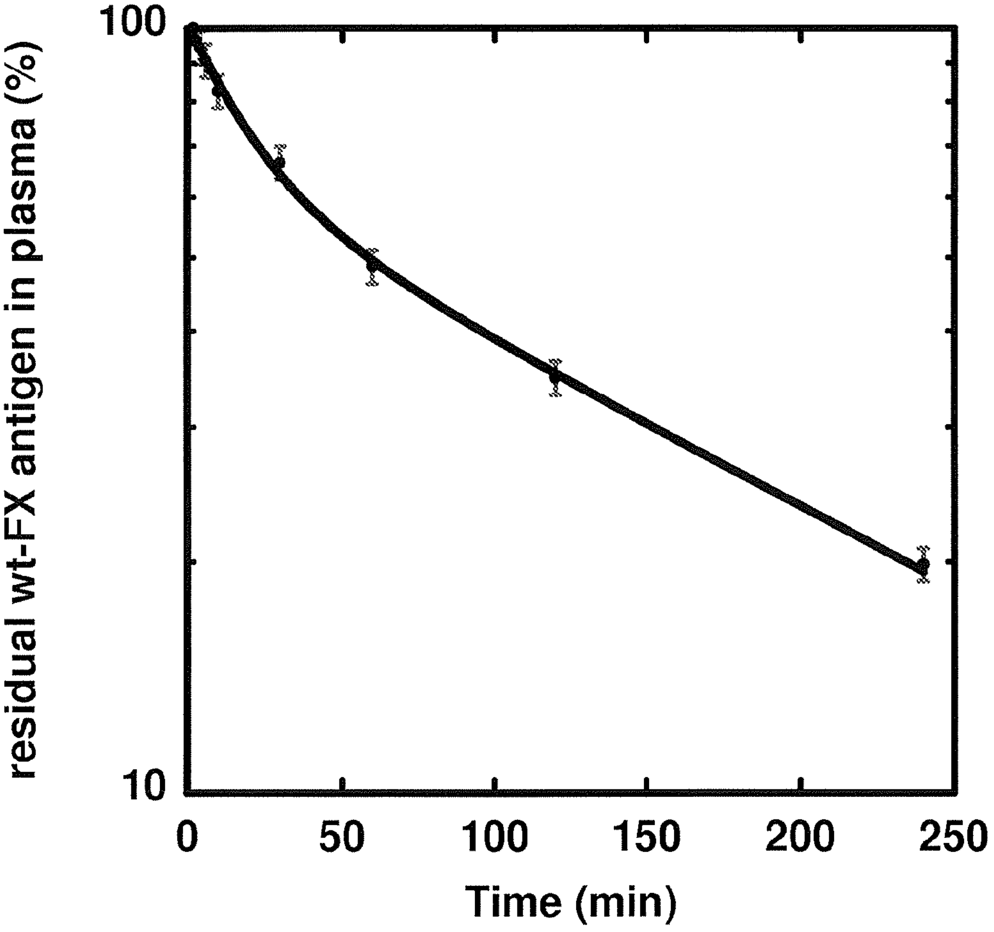

FIG. 11: Biphasic clearance of FX/AP176-194-N181A from plasma.

Mice were injected intravenously with purified FX/AP176-194-N181A (10 kg/mouse). At indicated time points blood sample were taken. The amount of residual FX/AP176-194-N181A antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

Figure 12:
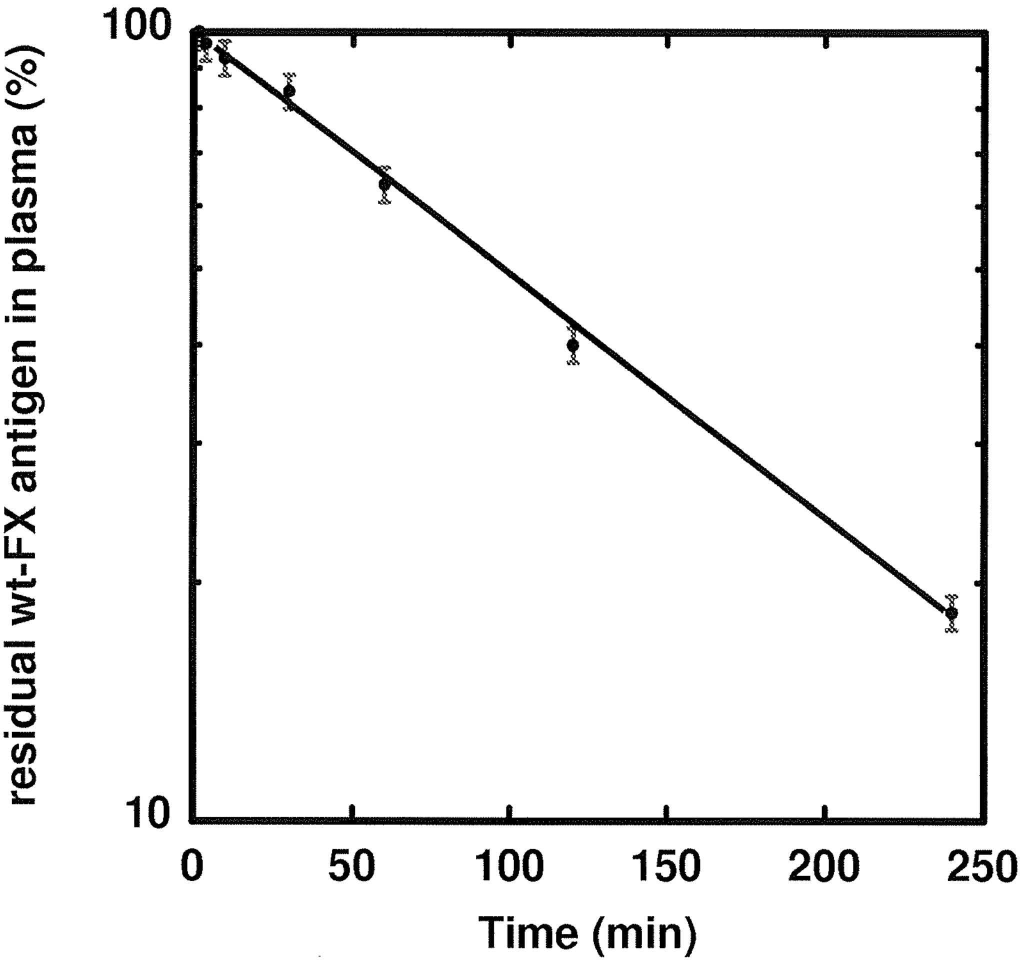

FIG. 12: Monophasic clearance of FX/AP176-194-N191A from plasma.

Mice were injected intravenously with purified FX/AP176-194-N191A (10 kg/mouse). At indicated time points blood sample were taken. The amount of residual FX/AP176-194-N191A antigen in plasma was quantified in an ELISA (see "Experimental Procedure"). Plotted is the percentage of residual antigen in plasma relative to the amount present 2 min after injection versus time after injection. Pharmacokinetic parameters derived from these data are summarized in Table I. Data represent mean values±S.D. of 3 mice for each time point.

EXAMPLE

Material & Methods

Material

Baby hamster kidneys (BHK) were from ATCC (Rockville, USA). Fetal calf serum (FCS) and bovine serum albumin (BSA protease free) were purchased from PAA Laboratories (Les Mureaux, France). Dulbecco's modified Eagle's/F12 medium, penicillin/streptomycin, fungizone (amphotericin B deoxycholate) were obtained from Invitrogen (Cergy Pontoise, France). Benzamidine and phenylsulfonylfluoride (PMSF) were from Calbiochem (Meudon, France). Methotrexate, vitamin K1, polyethyleneglycol 8000 (PEG) were purchased from Sigma (Saint Quentin Fallavier, France). N-abenzyloxycarbonyl-D-arginyl-L-arginine-p-nitroanilide-dihydrochloride (N-a-Z-D-Arg-Gly-Arg-p-NA) product name S-2765 was from Chromogenix (Mölndal, Sweden). L-alpha-phosphatidyl-L-serine (from bovine brain), and L-alpha-phosphatidylcholine (from egg-yolk) were from Avanti Polarlipids (Albaster, USA). QAE Sephadex A-50, HiTrap™ Q column, Heparin HiTrap column were obtained from GE Healthcare (Orsay, France). Anti protein C affinity matrix was purchased from Roche Diagnostics (Meylan, France).

Construction of Recombinant FX Derivatives

The mammalian expression plasmid pKG5 containing human factor X cDNA (Christophe, et al., 2001), the plasmid containing human insulin cDNA and the plasmid containing human protein C cDNA were used as templates for standard PCR mutagenesis to generate cDNA encoding respectively full-length human factor X, full-length human insulin and full length human protein with a C-terminal HPC-4 tag (residues EDQVDPRLIDGK, SEQ ID NO:27). The mutated full-length cDNAs' cloned into the expression vector pNUT were checked by DNA sequence analysis using the ABI PRISM Dye Terminator Cycle Sequencing Reaction Kit v3.1 (Applied Biosystems Applera, Courtaboeuf, France) on an ABI PRISM 310 DNA sequencer according to the manufacturer's specifications. The FX construct was used as a template for standard PCR mutagenesis (see primers table I) to generate cDNAs encoding factor X variants with partial deletions and specific mutations in the activation peptide named FX/AP176-194, FX/delPA-FpA, FX/AP-FpA, FX/AP 176-194-N 181A, FX/AP176-194-N191A, and FX/AP176-194-N181A-N191A (FIG. 4). The insulin construct was used as a template for standard PCR mutagenesis to generate cDNA encoding an insulin variant containing a polypeptide PP comprising the amino acid sequence ranging from positions 33 to 52 of SEQ ID NO:2 (activation peptide of factor X). Similarly, the protein C construct was used as a template to generate cDNAs encoding protein C variants (FIG. 5). The constructs cloned into the pNUT-expression vector were entirely sequenced.

TABLE I

Primers used to generate the different factor X variants

| Mutated Primers | Sequences (5' → 3' sens) |
|---|---|
| FX/$AP^{176-194}$ sens | CTGGAACGCCGGAAGAGGGACCTGCTTGACTTCAACCAGACGCAG (SEQ ID NO: 28) |

TABLE I-continued

Primers used to generate the different factor X variants

| Mutated Primers | Sequences (5' → 3' sens) |
|---|---|
| FX/AP$^{176-194}$ antisens | GTTGAAGTCCAGCAGGTCCCTCTTCCGACGTTCCAGTGTCTGTTT (SEQ ID NO: 29) |
| FX/delAP-FpA sens | GACTTTCTAGCTGAAGGAGGAGGCGTGCGTATCGTGGGAGGCCAGGAATGC (SEQ ID NO: 30) |
| FX/delAP-FpA antisens | CCTCCTCCTTCTGCTAGAAAGTCTCTCTTTCTGCGTTCCAGGGTCTGTTT (SEQ ID NO: 31) |
| FX/AP-FpA sens | GACTTTCTAGCTGAAGGAGGAGGCGTGCGTATCGTGGGAGGCCAGGAATGC (SEQ ID NO: 30) |
| FX/AP-FpA antisens | CCTCCTCCTTCTGCTAGAAAGTCCCTGGTCAGGTTGTTGTCG (SEQ ID NO: 32) |
| FX/AP$^{176-194-N181A}$ sens | CTTGACTTCGCCCAGACGCAGCCT (SEQ ID NO: 33) |
| FX/AP$^{176-194-N181A}$ antisens | AGGCTGCGTCTGGGGGAAGTCAAG (SEQ ID NO: 34) |
| FX/AP$^{176-194-N191A}$ sens | GGCGACAATGCTCTCACCAGGATCGT (SEQ ID NO: 35) |
| FX/AP$^{176-194-N191A}$ antisens | GATCCTGGTGAGAGCATTGTCGCCCCT (SEQ ID NO: 36) |

Obtention of Cell Lines Expressing the Recombinant Derivatives

The pNUT-constructs were transfected into Baby hamster kidney cells (BHK) using the jetPEI reactant (Qbiogen, Ozyme, France) as specified by the provider. After selection of transfected cells with medium containing methotrexate (Sigma) at a concentration of 100 μM, single clones were picked and propagated in selective medium to obtain stable cell lines. Production of factor X antigen was assayed by enzyme-linked immunosorbent assay (ELISA) using polyclonal antibodies against factor X conjugated and not with horseradish peroxidase obtained from Dako (Dakopatts, Glostrup, Denmark). Purified human plasma derived factor X (pd-FX) from Kordia (Leiden, The Netherlands) was used as reference. Production of insulin was assayed by the human insulin ELISA kit from Dako. Production of Protein C was assayed by two-site ELTSA with affinity purified mouse monoclonal antibody for coating (Roche, Meylan, France) and polyclonal antibodies against protein conjugated with horseradish peroxidase obtained from Dako. Cell lines producing factor X, insulin and protein C were selected.

Production and Purification of Recombinant Factor X, Insulin and Protein C Derivatives Stable cell lines producing recombinant factor X, insulin and protein C derivatives as well as wild-type factor X, insulin and protein C were maintained in 300 $cm^2$ flasks for protein production in DMEM/F-12 supplemented with 10% FCS, 50 μM methotrexate, 100 U/ml penicillin, 100 μg/ml streptomycin, and 5 μg/ml vitamin K1 (not for insulin). Protein of interest containing medium was harvested every 48 hours. Benzamidine and PMSF were added to a final concentration of 10 and 2 mM, respectively, and the medium centrifuged (6 000 g), passed over cellulose acetate membranes (0.45 μm) to eliminate cell debris, and stored at −20° C. until use. Conditioned medium was thawed at 37° C. EDTA was added to a final concentration of 5 mM. The medium was diluted in distilled water and in Tris (pH 7.4), to bring the final Tris and NaCl concentration to 25 and 60 mM, respectively. The mixture was then stirred at room temperature for 30 min with QAE Sephadex A-50 beads to achieve a final concentration of 0.25% (wt/v). Beads were washed before elution with 50 mM Tris (pH 7.4), 500 mM NaCl, and 10 mM benzamidine. Recombinant proteins contained in the eluted fractions (ELISA) were immediately dialyzed against 25 mM Tris (pH 7.4), and 100 mM NaCl, containing 10 mM benzamidine, and stored at −20° C. before use. Concentrated proteins were thawed at 37° C. Calcium was added to a final concentration of 5 mM. Purification of recombinant proteins was performed by affinity-chromatography using HPC-4-agarose (Roche, Meylan, France) as instructed by the provider. 1 h prior to use as a zymogen, factor X derivatives were incubated with 1 mM PMSF to neutralize any trace of activated factor X that may have been generated during production or purification of the recombinant protein. Same treatment was applied to protein C derivatives. Control experiments indicated that after 30 min in Tris-HCl buffer, PMSF was fully hydrolyzed and would not interfere with other reactions. Protein purity was assessed using 10% SDS-polyacrylamide gel electrophoresis analysis of the recombinant proteins under reducing (100 mM dithiothreitol, final concentration) and non-reducing conditions followed by staining with Coomassie Brilliant Blue R-250. Factor X, insulin and protein C identification was carried out after the purified recombinant proteins were reduced and loaded onto a 10% SDS-polyacrylamide gel. The resolved proteins were transferred to an Immobilon membrane and blotted using polyclonal antibodies against factor X, insulin and protein C conjugated with horseradish peroxydase (Dakopatts, Glostrup, Denmark). The purified derivatives were aliquoted and stored at −80° C. until use. The concentration of the aliquot is estimated by its absorbance at 280 nm, taking 1.16, 1.05, and 1.45 to be the extinction coefficient (E280 nm 0.1%) of factor X, insulin, and protein C.

Mice

Wild-type male mice on a C57BL/6 background (Janvier, Le Genest-St-Isle, France) were used throughout this study and were between 8 and 9 weeks of age. Housing and experiments were done as recommended by French regulations and the experimental guidelines of the European Community. 24 mice were used for each clearance exploration.

Clearance, Recovery, and Biodistribution of Factor X Derivatives in Mice

Nonanesthetized mice were placed in a restraining device and their tail was immersed in a water bath at 40° C. for 3 min. Then, 200 μl of factor X derivatives diluted at 50 μg/ml in Phosphate-buffered saline (PBS) were injected into the mouse tail vein. At different time points (2, 6, 10, and 30 min and 1, 2, 4 and 8 h after injection) mice were anesthetized by intraperitoneal injection of sodium pentobarbital (60 mg/kg; Ceva Sante Animale, Libourne, France) and blood was collected from the retro-orbital venous plexus into plastic tubes containing trisodium citrate (9 volumes of blood to 1 volume of 0.138 M trisodium citrate). Three mice were used for each time point, and each mouse was bled only once. To obtain platelet poor plasma, blood samples were centrifuged at 1000 g for 20 minutes at room temperature. Factor X derivatives concentration in plasma was measured with an immunosorbent assay using a mouse monoclonal antibody called HPC-4 (Roche) coated in carbonate buffer (pH 9.6) and a horseradish peroxydase conjugated polyclonal antibody anti-human factor X (Dako). Recombinant purified and quantified wild-type factor X HPC4 tagged (see above) was used as a reference. Results were expressed as percentage of recombinant human factor X injected. For biodistribution experiments and recovery determination, highly purified recombinant FX variants were labeled with $Na^{125}I$ (Perkin-Elmer, Courtaboeuf, France) using Iodo Gen (Pierce Chemical Co., Rockford, Ill., USA) as described (Fracker and Speck, BBRC 1978). Specific radioactivities varied from 2 to $10\times10^4$ cpm/μg of FX variants. Free iodine in final preparations was below 5% as determined by precipitation with 20% trichloroacetic acid. Recovery represents the percentage of FX present in plasma 5 min after injection relative to he amount injected.

Clearance of Protein C and Insulin Variants in Mice

For each protein C and insulin variants, 24 male WT mice, 8-weeks old, is used. 10 μg of purified recombinant protein diluted in PBS is injected per mouse via the tail vein. At different time-points after injection mice is anesthetized with tribromoethanol (60 mg/kg body weight), and blood is collected by retro-orbital venous sampling on hirudin (Diagnostica Stago, Asnieres, France) (100 UI, final concentration). Three mice is used per time-point and each mouse is bled only once. Plasma is prepared and analyzed for residual injected antigen concentration by ELISA or by the residual activity.

Data Analysis

Clearance curves refer to the amount of residual factor X, protein C and insulin derivatives antigen in mouse plasma relative to the amount injected (% of the concentration injected) as a function of time. Data were fitted either to a monoexponential equation:

$$Cp=Ae-\alpha t \qquad \text{equation 1}$$

or a biexponential equation:

$$Cp=Ae-\alpha t+Be-\beta t \qquad \text{equation 2}$$

Parameters A, α, B et β were determined using KaleidaGraph software (KaleidaGraph version 4.02. for Mac OS X, Synergy Software, Reading, USA). Cp refers to the amount of residual factor X derivative in plasma relative to the amount injected. These parameters are needed to calculate the mean residence time (MRT).

In a biphasic clearance process:

$$MRT=(A/\alpha^2+B/\beta^2)/(A/\alpha+B/\beta) \qquad \text{equation 3}$$

In a monophasic clearance mechanism:

$$MRT=(A/\alpha^2)/(A/\alpha) \qquad \text{equation 4}$$

Furthermore, α and β were used to calculate half-lives of the initial and terminal phase, respectively, employing T½α=ln 2/α, et T½β=ln 2/β.

Thrombin Generation Assay

Thrombin generation was measured according to the method described by Hemker et al (Hemker H C, Giesen P, Al Dieri R, et al. Pathophysiol Haemost Thromb 2003; 33:4-15), in a Fluoroscan Ascent fluorometer (Thermolabsystems OY, Helsink, Finland) equipped with a dispenser. Briefly, 80.11 of plasma supplemented with either saline (control) or with indicated concentration of anticoagulant fondaparinux (Arixtra®, GlaxoSmithKline, Brentford, UK) and various concentrations of recombinant factor X derivatives were dispensed into round-bottom 96-well microtiter plates. Twenty μl of a mixture containing TF (recombinant lipidated human tissue factor, Innovin®, obtained from Dade Behring) and phospholipids (PL) vesicles was added to the plasma sample to obtain a final concentration of 1 pM TF and 4 μM PL vesicles. PL vesicles prepared from L-α-Phosphatidyl-L-serine (PS) and L-α-phosphatidylcholine (PC) (Avanti Polarlipids, Albaster, Ala., USA) and of nominal 100 nm-diameter (PC:PS, 3:1) were synthesized by the method of membrane extrusion (Olson, F., Hunt, C. A., Szoka, F. C., Vail, W. J., and Papahadjopoulos, D. (1979) *Biochim Biophys Acta* 557(1), 9-23). Phospholipid concentration was determined by phosphate analysis. Finally, thrombin generation was triggered by adding 20 μl of starting reagent containing fluorogenic substrate and $CaCl_2$. Fluorogenic substrate 1-1140 (Z-Gly-Gly-Arg-AMC) was from Bachem AG (Bubendorf, Switzerland). Kinetics of thrombin generation in clotting plasma was monitored for 60 min at 37° C. using a calibrated automated thrombogram and analyzed using the Thrombinoscope™ software (Thrombinoscope B.V., Maastricht, the Netherlands). Three wells were needed for each experiment, two wells to measure thrombin generation of a plasma sample and one well for calibration. All experiments were carried out in triplicate and the mean value was reported. Endogenous thrombin potential (ETP), i.e. area under the curve, peak thrombin, and lag time for thrombin detection determined.

Results

Biphasic Clearance of Recombinant Wild-Type Factor X

To investigate the clearance of factor X from plasma, mice were injected intravenously with recombinant wild-type factor X. At indicated time points after injection, mice were bled and plasma was analyzed for factor X antigen. Graphic representation of the antigen values as function of time after injection revealed that wild-type factor X was eliminated from the blood with a biphasic clearance characterized by a rapid and a slow half lives of 43 and 305 min, respectively (FIG. 6). Furthermore, MRT was calculated to be 380 min (Table II).

TABLE II

Pharmacokinetic parameters describing the clearance and recovery of wt-factor X and its variants from plasma.
N.A. = not applicable. N.D. = not determined

| | Recovery | MRT | $T_{1/2}\alpha$ | $T_{1/2}\beta$ |
|---|---|---|---|---|
| wt-FX | 69% | 380 min | 43 min | 304 min |
| FX/delAP-FpA | N.D. | 58 min | 40 min | N.A. |
| FX/AP-FpA | N.D. | 345 min | 38 min | 266 min |
| $FX/AP^{176-194}$ | 67% | 330 min | 44 min | 255 min |
| $FX/AP^{176-194\text{-}N181A\text{-}N191A}$ | 29% | 69 min | 48 min | N.A. |

TABLE II-continued

Pharmacokinetic parameters describing the clearance and recovery of wt-factor X and its variants from plasma.
N.A. = not applicable. N.D. = not determined

| | Recovery | MRT | $T_{1/2}\alpha$ | $T_{1/2}\beta$ |
|---|---|---|---|---|
| $FX/AP^{176\text{-}194\text{-}N181A}$ | 61% | 191 min | 15 min | 140 min |
| $FX/AP^{176\text{-}194\text{-}N191A}$ | 76% | 140 min | 96 min | N.A. |

Monophasic Clearance of Recombinant FX/delAP-FpA

To determine the role of the activation peptide in the kinetic of clearance of factor X, a factor X variant deleted of its activation peptide was designed, produced and purified. This variant called FX/delAP-FpA has no factor X activation peptide but instead 10 residues corresponding to the carboxy-terminal end of the fibrinopeptide A. The sequence of the fibrinopeptide A residues is different from the corresponding residues present in FX activation peptide. In contrast to wild-type factor X, after injection to mice FX/delAP-FpA showed a monophasic pattern of clearance with an apparent half-life of 40 minutes (FIG. 7). In addition, MRT was 6-fold reduced for the truncated molecule compared with wild-type factor X (Table II). In conclusion, these data suggest that the activation peptide of factor X has a crucial role in the rate of factor X clearance in plasma.

Biphasic Clearance of Recombinant FX/AP-FPA

To verify that the effect observed on the clearance pattern and pharmacokinetic parameters of FX/delAP-FpA was not due to the presence of the fibrinopeptide A residues but to the deletion of the factor X activation peptide, FX/AP-FpA was designed, produced, purified and characterized. This factor X variant contains the 52 residues of the factor X activation peptide linked at their carboxy terminal end to 10 residues the fibrinopeptide A. The purified variant was administered to mice by tail vein injection. A clearance pattern similar to wild-type factor X was observed (FIG. 8). As summarized in Table II, similar pharmacokinetic parameters were obtained for this variant and wt-FX. Thus, the fast rate of FX/delAP-FpA clearance previously observed (see above) was independent of the presence of the FIX sequence but was due to the absence of the 52 residues of the FX activation peptide.

Biphasic Clearance of Recombinant FX/AP176-194

It was of interest to identify the residues of the activation peptide contributing to the factor X clearance. To this end, a factor X variant called FX/AP176-194 with only 19 residues of the carboxy-terminal end of the factor X activation peptide was constructed. Purified variant was administered to mice by tail vein injection. Mice were bled at different time points and plasma was analyzed for factor X antigen. These experiments revealed that FX/AP176-194 was cleared from plasma in a similar manner to wild-type factor X (FIG. 9). Indeed, similar pharmacokinetic parameters could be calculated from the experimental data (Table II). These data demonstrate that residues within the carboxy-terminal end of factor X activation peptide play a crucial role in the rate of factor X clearance.

Involvement of N-Glycosylation in the Activation Peptide in the Clearance of FX from the Circulation.

Since the carboxy-terminal end of factor X contains two N-glycosylation sites (Asn 181 and 191), the possible role of these post-translational modifications on the circulatory lifetime of factor X was studied using FX/AP176-194 mutated at one or both N-glycosylation sites. Two single- and one double-mutated variants called FX/AP176-194-N181A, FX/AP176-194-N191A, and FX/AP 176-194-N 181A-N191A. were produced, purified and their clearance studied.

The double mutant FX/AP176-194-N181A-N191A was cleared from the circulation more rapidly than wild-type factor X and interestingly with a clearance pattern similar to FX/delAP-FpA, the factor X variant with no factor X activation peptide (FIG. 10). As indicated in Table II, similar pharmacokinetic parameters were obtained for FX/AP176-194-N181A-N191A and FX/delAP-FpA. These data demonstrate that N-glycosylations at position 181 and 191 in the activation peptide play a crucial role in factor X survival. For the variant FX/AP176-194-N181A, a biphasic clearance was observed (FIG. 11) like for the wild-type factor X. However its elimination from the circulation was faster than for wt-FX as indicated table II. For the variant FX/AP176-194-N191A, a monophasic clearance was observed (FIG. 12) like for FX/delAP-FpA. In contrast its elimination was longer than for FX/delAP-FpA but with a similar MRT compared with FX/AP176-194-N181A. These data indicate that N-glycosylation at position 181 is responsible of the monophasic pattern of factor X clearance while N-glycosylation at position 191 is responsible of the biphasic pattern. Furthermore, both N-glycosylations play an important role in the pharmacokinetic parameters of factor X.

REFERENCES

Throughout this application, various references describe the state of the art to which this invention pertains. The disclosures of these references are hereby incorporated by reference into the present disclosure.

Arnljots B, Bergqvist D, Dahlbäck B. Inhibition of microarterial thrombosis by activated protein C in a rabbit model. Thromb Haemost. 1994; 72(3):415-20.

Bauer K A. New anticoagulants. Curr Opin Hematol. 2008; 15(5):509-15.

Bernard G R, Vincent J L, Laterre P F, LaRosa S P, Dhainaut J F, Lopez-Rodriguez A, Steingrub J S, Garber G E, Helterbrand J D, Ely E W, Fisher C J Jr. Efficacy and safety of recombinant human activated protein C for severe sepsis. N Engl J. Med. 2001; 344(10):699-709.

Borensztajn K, Peppelenbosch M P, Spek C A. Factor Xa: at the crossroads between coagulation and signaling in physiology and disease. Trends Mol. Med. 2008; 14(10):429-40.

Brady G, Jantzen H M, Bernard H U, Brown R, Schutz G, Hashimoto-Gotoh T. New cosmid vectors developed for eukaryotic DNA cloning. Gene. 1984 February; 27(2):223-32.

Brink M F, Bishop M D, Pieper F R. Developing efficient strategies for the generation of transgenic cattle which produce biopharmaceuticals in milk. Theriogenology. 2000; 53(1):139-48.

Camire R M, Larson P J, Stafford D W, High K A. Enhanced gamma-carboxylation of recombinant factor X using a chimeric construct containing the prothrombin propcptide. Biochemistry. 2000; 39(46):14322-9.

Chesebro J H, Webster M W, Zoldhelyi P, Roche P C, Badimon L, Badimon J J. Antithrombotic therapy and progression of coronary artery disease. Antiplatelet versus antithrombins. Circulation. 1992; 86(6 Suppl):III100-10.

Christophe O D, Lenting P J, Cherel G, Boon-Spijker M, Layergne J M, Boertjes R, Briquel M E, de Goede-Bolder A, Goudemand J, Gaillard S, d'Oiron R, Meyer D, Mertens K. Functional mapping of anti-factor IX inhibitors developed in patients with severe hemophilia. Blood. 2001; 98(5):1416-23.

Comp P C, Esmon C T. Generation of fibrinolytic activity by infusion of activated protein C into dogs. J Clin Invest. 1981; 68(5):1221-8.

Esmon C T. Regulation of blood coagulation. Biochim Biophys Acta. 2000; 1477(1-2):349-60.
Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.
Gresele P, Momi S, Berrettini M, Nenci G G, Schwarz H P, Semeraro N, Colucci M. Activated human protein C prevents thrombin-induced thromboembolism in mice. Evidence that activated protein c reduces intravascular fibrin accumulation through the inhibition of additional thrombin generation. J Clin Invest. 1998; 101(3):667-76.
Gruber A, Griffin J H, Harker L A, Hanson S R. Inhibition of platelet-dependent thrombus formation by human activated protein C in a primate model. Blood. 1989; 15; 73(3): 639-42.
Gustafsson D, Bylund R, Antonsson T, Nilsson I, Nyström J E, Eriksson U, Bredberg U, Teger-Nilsson AC. A new oral anticoagulant: the 50-year challenge. Nat Rev Drug Discov. 2004; 3(8):649-59.
Hanson S R, Griffin J H, Harker L A, Kelly A B, Esmon C T, Gruber A. Antithrombotic effects of thrombin-induced activation of endogenous protein C in primates. J Clin Invest. 1993; 92(4):2003-12.
Harenberg J. Development of new anticoagulants: present and future. Semin Thromb Hemost. 2008; 34(8):779-93.
Jang Y, Guzman L A, Lincoff A M, Gottsauner-Wolf M, Forudi F, Hart C E, Courtman D W, Ezban M, Ellis S G, Topol E J. Influence of blockade at specific levels of the coagulation cascade on restenosis in a rabbit atherosclerotic femoral artery injury model. Circulation. 1995; 92(10):3041-50.
Joyce D E, Gelbert L, Ciaccia A, DeHoff B, Grinnell B W. Gene expression profile of antithrombotic protein c defines new mechanisms modulating inflammation and apoptosis. J Biol. Chem. 2001; 276(14):11199-203.
Kurz K D, Smith T, Wilson A, Gerlitz B, Richardson M A, Grinnell B W. Antithrombotic efficacy in the guinea pig of a derivative of human protein C with enhanced activation by thrombin. Blood. 1997; 89(2):534-40.
Khoo C W, Tay K H, Shantsila E, Lip G Y. Novel oral anticoagulants. Int J Clin Pract. 2009; 63(4):630-41.
Kuwana Y, Asakura Y, Utsunomiya N, Nakanishi M, Arata Y, Itoh S, Nagase F, Kurosawa Y. Expression of chimeric receptor composed of immunoglobulin-derived V regions and T-cell receptor-derived C regions. Biochem Biophys Res Commun. 1987 Dec. 31; 149(3):960-8.
Louvain-Quintard V B, Bianchini E P, Calmel-Tareau C, Tagzirt M, Le Bonniec B F. Thrombin-activable factor X reestablishes an intrinsic amplification in tenase-deficient plasmas. J Biol. Chem. 2005; 280(50):41352-9.
Mason J O, Williams G T, Neuberger M S. Transcription cell type specificity is conferred by an immunoglobulin VH gene promoter that includes a functional consensus sequence. Cell. 1985 June; 41(2):479-87.
Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.
Mizukami T, Itoh S. A new SV40-based vector developed for cDNA expression in animal cells. J Biochem (Tokyo). 1987 May; 101(5):1307-10.
Mizutani A, Okajima K, Uchiba M, Noguchi T. Activated protein C reduces ischemia/reperfusion-induced renal injury in rats by inhibiting leukocyte activation. Blood. 2000; 95(12):3781-7.
O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527-31.
Rezaie A R. Vitronectin functions as a cofactor for rapid inhibition of activated protein C by plasminogen activator inhibitor-1. Implications for the mechanism of profibrinolytic action of activated protein C. J Biol. Chem. 2001; 276(19):15567-70.
Rudolph A E, Mullane M P, Porche-Sorbet R, Miletich J P. Expression, purification, and characterization of recombinant human factor X. Protein Expr Purif. 1997; 10(3):373-8.
Taylor F B Jr, Chang A, Esmon C T, D'Angelo A, Vigano-D'Angelo S, Blick K E. Protein C prevents the coagulopathic and lethal effects of *Escherichia coli* infusion in the baboon. J Clin Invest. 1987; 79(3):918-25.
Toso R, Zhu H, Camire R M. The conformational switch from the factor X zymogen to protease state mediates exosite expression and prothrombinase assembly. J Biol. Chem. 2008; 283(27):18627-35.
Sakamoto T, Ogawa H, Yasue H, Oda Y, Kitajima S, Tsumoto K, Mizokami H. Prevention of arterial reocclusion after thrombolysis with activated protein C. Comparison with heparin in a canine model of coronary artery thrombosis. Circulation. 1994; 90(1):427-32.

The invention claimed is:

1. A chimeric thrombin-cleavable derivative of factor X, wherein at least one of arginine, lysine and serine of the chimeric derivative of factor X corresponding to residues at positions 387, 391 and 419, respectively, of SEQ ID NO:1 is replaced by alanine, and wherein a native activation peptide of the factor X is replaced by a fusion protein comprising a first polypeptide comprising an amino acid sequence ranging from positions 33 to 52 of SEQ ID NO: 2, wherein asparagine at at least one of positions 39 and 49 is N-glycosylated; and a second polypeptide comprising an amino acid sequence ranging from positions 7 to 16 of SEQ ID NO: 4 including variants thereof wherein the glycine at position 14 of SEQ ID NO: 4 is replaced by valine, phenylalanine or alanine and/or the valine at position 15 of SEQ ID NO: 4 is replaced by proline.

2. The chimeric thrombin-cleavable derivative of factor X of claim 1 wherein:

i) isoleucine corresponding to a residue at position 235 of SEQ ID NO:1 is replaced by alanine, serine or leucine and/or ii) valine corresponding to a residue at position 236 of SEQ ID NO:1 is replaced by phenylalanine or alanine.

3. A chimeric derivative of factor X of claim 1, wherein arginine and lysine of the chimeric derivative of factor X corresponding to residues at positions 387 and 391 of SEQ ID NO:1 are replaced by alanine.

4. A chimeric derivative of factor X of claim 1, wherein serine of the chimeric derivative of factor X corresponding to residue at position 419 of SEQ ID NO:1 is replaced by alanine.

5. The chimeric thrombin-cleavable derivative of factor X of claim 1, wherein asparagine at each of positions 39 and 49 is N-glycosylated.

6. The chimeric thrombin-cleavable derivative of factor X of claim 3, wherein each of positions 387, 391, and 419 of SEQ ID NO:1 is replaced by alanine.

7. The chimeric thrombin-cleavable derivative of factor X of claim 1, wherein i) asparagine at each of positions 39 and 49 is N-glycosylated and ii) each of positions 387, 391, and 419 of SEQ ID NO:1 is replaced by alanine.

8. A method for the treatment of clotting pathologies of the hemorrhagic type in a subject in need thereof, comprising the step of administering to the subject the chimeric derivative of factor X of claim 1.

9. A method for the treatment of haemophilias A or B in a subject in need thereof, comprising the step of administering to the subject the chimeric derivative of factor X of claim 1.

10. A method for the treatment of bleeding induced by low molecular weight heparins (LMWH) or by an anticoagulant targeting factor Xa in a subject in need thereof, comprising the step of administering to the subject the chimeric derivative of factor X of claim 1.

11. A nucleic acid molecule encoding the chimeric thrombin-cleavable derivatives of claim 1.

* * * * *